United States Patent
Lin et al.

(10) Patent No.: US 8,722,156 B2
(45) Date of Patent: May 13, 2014

(54) LIQUID CRYSTAL COMPOUND AND LIQUID CRYSTAL DISPLAY

(71) Applicant: Industrial Technology Research Institute, Hsinchu (TW)

(72) Inventors: Jian-Wen Lin, Luzhu Township (TW); Chun-Ming Wu, Banqiao (TW); Shih-Hsien Liu, Jhubei (TW); Kung-Lung Cheng, Hsinchu (TW); Chih-Lung Chin, Longtan Township (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 13/871,618

(22) Filed: Apr. 26, 2013

(65) Prior Publication Data

US 2013/0235320 A1 Sep. 12, 2013

Related U.S. Application Data

(63) Continuation-in-part of application No. 13/340,257, filed on Dec. 29, 2011, now Pat. No. 8,486,497.

(30) Foreign Application Priority Data

Oct. 24, 2011 (TW) .............................. 100138436 A
Oct. 12, 2012 (TW) .............................. 101137606 A

(51) Int. Cl.
| | |
|---|---|
| C09K 19/12 | (2006.01) |
| C09K 19/18 | (2006.01) |
| C09K 19/20 | (2006.01) |
| C09K 19/22 | (2006.01) |
| G02F 1/1333 | (2006.01) |
| C07C 255/54 | (2006.01) |
| C07C 255/55 | (2006.01) |
| C07C 69/78 | (2006.01) |
| C07C 233/66 | (2006.01) |
| C07C 25/24 | (2006.01) |
| C07C 43/225 | (2006.01) |

(52) U.S. Cl.
USPC ................. 428/1.1; 252/299.66; 252/299.67; 558/416; 560/65; 564/161; 564/184; 570/128; 570/129

(58) Field of Classification Search
CPC .... C07C 25/24; C07C 255/54; C07C 255/55; C07C 233/66; C07C 43/225; C07C 69/78; C09K 19/12; C09K 19/16; C09K 19/18; C09K 19/20; C09K 19/2007; C09K 19/2014; C09K 19/22; C09K 19/05; G02F 1/13332; G02F 1/13333

USPC ............ 560/65; 564/184, 161; 570/131, 128, 570/129; 252/299.01, 299.66, 299.67; 558/416; 428/1.1
See application file for complete search history.

(56) References Cited

U.S. PATENT DOCUMENTS

| | | | |
|---|---|---|---|
| 7,108,895 B2 | 9/2006 | Yokokouji et al. | |
| 8,486,497 B2 * | 7/2013 | Lin et al. | .................. 428/1.1 |
| 2011/0193022 A1 | 8/2011 | Tanaka et al. | |

FOREIGN PATENT DOCUMENTS

| | | |
|---|---|---|
| DE | 10241721 A1 | 4/2003 |
| JP | 10-45642 A | 2/1998 |
| TW | I314577 B | 6/1998 |
| WO | WO 2010/047260 A1 | 4/2010 |

OTHER PUBLICATIONS

Wu, et al., "Polarized UV Spectroscopy of Conjugated Liquid Crystals", Journal of Applied Physics 68, vol. 1, Jul. 1, 1990, pp. 78-85.
Sun, et al., "High Birefringence Phenyl Tolane Positive Compounds for Dual Frequency Liquid Crystals", Liquid Crystals, vol. 36, No. 12, Dec. 2009, pp. 1401-1408.
Wen et al., "Dielectric Heating Effects of Dual-Frequency Liquid Crystals", Applied Physics Letters 86, pp. 231104-1 to 231104-3, (2005).
Xianyu, et al., "High Birefringence and Large Negative Dielectric Anistropy Phenyl-tolane Liquid Crystals", Liquid Crystals, vol. 34, No. 12, Dec. 2007, pp. 1473-1478.

* cited by examiner

*Primary Examiner* — Shean C Wu
(74) *Attorney, Agent, or Firm* — Birch, Stewart, Kolasch & Birch, LLP

(57) ABSTRACT

An embodiment of the disclosure provides a liquid crystal compound having the following formula:

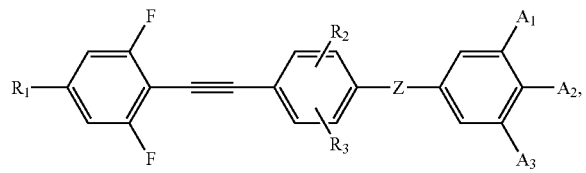

wherein $A_1$, $A_2$, and $A_3$ are independently hydrogen, halogen, cyano, thiocyanato, or —$OCF_3$; $R_1$ is hydrogen, halogen, $C_1$-$C_{12}$ alkyl, $C_1$-$C_{12}$ alkoxy, $C_1$-$C_{12}$ haloalkly, $C_2$-$C_{12}$ alkenyl, or $C_2$-$C_{12}$ alkynyl; $R_2$ and $R_3$ are independently hydrogen, halogen, $C_1$-$C_6$ alkyl, $C_1$-$C_6$ haloalkly, cyano, thiocyanato, or —$OCF_3$; and Z is a single bond, —O—, —$CH_2O$—, —C(O)O—, —OCO—, —C(O)NH—, or —CH=CH—. In another embodiment, a liquid crystal display including the liquid crystal compound is also provided.

7 Claims, 1 Drawing Sheet

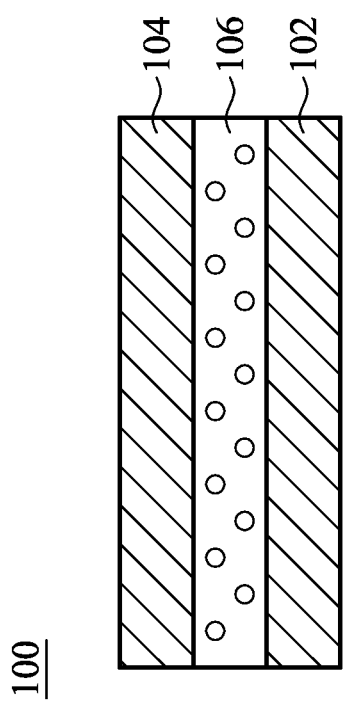

LIQUID CRYSTAL COMPOUND AND LIQUID CRYSTAL DISPLAY

CROSS REFERENCE TO RELATED APPLICATIONS

This application is a Continuation-In-Part of pending U.S. patent application Ser. No. 13/340,257, filed Dec. 29, 2011 and entitled "Liquid crystal compound and liquid crystal display", which claims priority of Taiwan Patent Application No. 100138436, filed on Oct. 24, 2011, the entirety of which is incorporated by reference herein.

This application claims priority of Taiwan Patent Application No. 101137606, filed on Oct. 12, 2012, the entirety of which is incorporated by reference herein.

TECHNICAL FIELD

The present invention relates to a liquid crystal compound, and in particular relates to a liquid crystal compound having high dielectric anisotropy.

BACKGROUND

As technology has rapidly developed, various portable electronic products such as mobile phones, laptops, digital cameras, PDA, MP3, MP4, and etc. have become very important in modern day life. Meanwhile, advantages of liquid crystal displays include a small-size, light-weight, and low electricity consumption, and thus they have been frequently used in recent years. In a liquid crystal display, a liquid crystal material, which will affect the performance of a device using the same, plays an important role in the development of liquid crystal displays.

A good liquid crystal material should be, for example, stable toward water, air, heat, and light and have an appropriate dielectric anisotropy ($\Delta\in$), birefringence ($\Delta n$), and elastic constant ($K_{ii}$). An appropriate liquid crystal material can be chosen depending on particular requirements of liquid crystal displays.

Dielectric anisotropy ($\Delta\in$) refers to the difference between a dielectric coefficient in a parallel direction ($\in_\parallel$) and a dielectric coefficient in a vertical direction ($\in_\perp$). In other words, $\Delta\in=\in_\parallel-\in_\perp$. Therefore, when $\in_\parallel>\in_\perp$, it is called a positive dielectric anisotropy liquid crystal. When $\in_\parallel<\in_\perp$, it is called a negative dielectric anisotropy liquid crystal. The value (positive or negative) of the dielectric anisotropy determines whether the liquid crystal is parallel or vertical to the electric field and whether light will pass through the liquid crystal layer or not. In addition, the dielectric anisotropy of a liquid crystal and driving voltage can be presented by the following formula:

$$V_{th}=\pi\left(\frac{K_{ii}}{\Delta\varepsilon}\right)^{1/2}$$

The larger the dielectric anisotropy, the lower the driving voltage. Therefore, the liquid crystal display having high dielectric anisotropy can work with a lower voltage. However, diamagnetic anisotropies of most liquid crystal materials are smaller than 3.5, which is not satisfactory for modern day liquid crystal display use.

Therefore, a liquid crystal material having high dielectric anisotropy is desirable to decrease driving voltage.

SUMMARY

An embodiment of the disclosure provides a liquid crystal compound having the following formula:

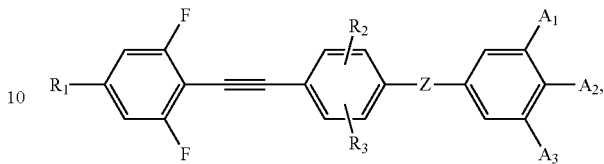

wherein $A_1$, $A_2$, and $A_3$ are independently hydrogen, halogen, cyano, thiocyanato, or —$OCF_3$; $R_1$ is hydrogen, halogen, $C_1$-$C_{12}$ alkyl, $C_1$-$C_{12}$ alkoxy, $C_1$-$C_{12}$ haloalkly, $C_2$-$C_{12}$ alkenyl, or $C_2$-$C_{12}$ alkynyl; $R_2$ and $R_3$ are independently hydrogen, halogen, $C_1$-$C_6$ alkyl, $C_1$-$C_6$ haloalkly, cyano, thiocyanato, or —$OCF_3$; and Z is a single bond, —O—, —$CH_2O$—, —C(O)O—, —OCO—, —C(O)NH—, or —CH=CH—.

Another embodiment of the disclosure provides a liquid crystal display, comprising: a first substrate; a second substrate disposed opposite to the first substrate; and a liquid crystal layer disposed between the first substrate and the second substrate, wherein the liquid crystal layer comprises the above described liquid crystal compound.

A detailed description is given in the following embodiments with reference to the accompanying drawings.

BRIEF DESCRIPTION OF THE DRAWINGS

The present disclosure can be more fully understood by reading the subsequent detailed description and examples with references made to the accompanying drawings, wherein:

FIG. 1 is cross section of a liquid crystal display according to one embodiment of the disclosure.

DETAILED DESCRIPTION

The following description is of the best-contemplated mode of carrying out the disclosure. This description is made for the purpose of illustrating the general principles of the disclosure and should not be taken in a limiting sense. The scope of the disclosure is best determined by reference to the appended claims.

Moreover, the formation of a first feature over and on a second feature in the description that follows may include embodiments in which the first and second features are formed in direct contact, and may also include embodiments in which additional features may be formed between the first and second features, such that the first and second features may not be in direct contact.

A liquid crystal compound may have following formula:

(I)

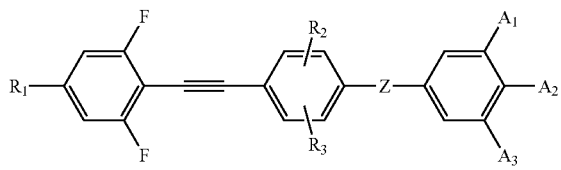

wherein $A_1$, $A_2$, and $A_3$ are independently hydrogen, halogen, cyano, thiocyanato, or —$OCF_3$; $R_1$ is hydrogen, halogen, $C_1$-$C_{12}$ alkyl, $C_1$-$C_{12}$ alkoxy, $C_1$-$C_{12}$ haloalkly, $C_2$-$C_{12}$ alkenyl, or $C_2$-$C_{12}$ alkynyl; $R_2$ and $R_3$ are independently hydrogen, halogen, $C_1$-$C_6$ alkyl, $C_1$-$C_6$ haloalkly, cyano, thiocyanato, or —$OCF_3$; and Z is a single bond, —O—, —$CH_2O$—, —C(O)O—, —OCO—, —C(O)NH—, or —CH═CH—. The liquid crystal compound may have high dielectric anisotropy. In one embodiment, the dielectric anisotropy is above 40. In another embodiment, the dielectric anisotropy is between 40 and 90. In one embodiment, $A_1$, $A_2$, and $A_3$ are independently halogen or cyano. In another embodiment, $R_1$ is $C_1$-$C_{12}$ alkyl or $C_1$-$C_{12}$ alkoxy. In still another embodiment, $R_2$ and $R_3$ are independently hydrogen or fluorine. In still another embodiment, Z is —C(O)O— or —C(O)NH—.

In one embodiment, the liquid crystal compound of formula (I) may further have following formula (II):

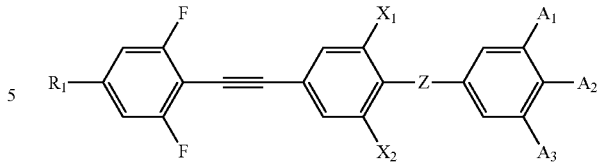

wherein $A_1$, $A_2$, $A_3$, $R_1$ and Z may be the same with formula (I) described above. $X_1$ and $X_2$ are independently hydrogen, fluorine, cyano, thiocyanato, or —$OCF_3$.

Table 1 presents specific examples of the liquid crystal compound (I) or (II). However, these are, of course, merely examples and are not intended to be limiting.

TABLE 1

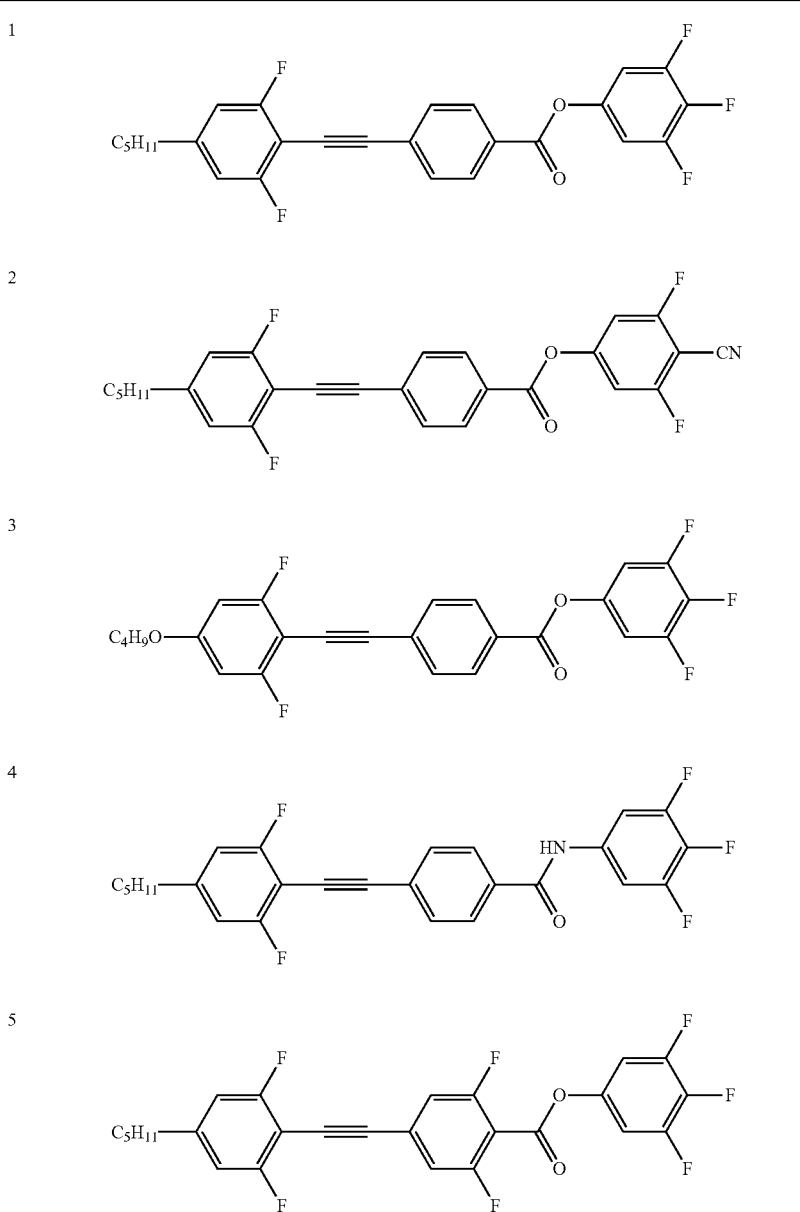

TABLE 1-continued

TABLE 1-continued
| 13 | 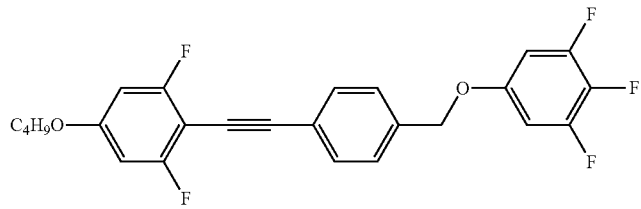 |
| 14 | 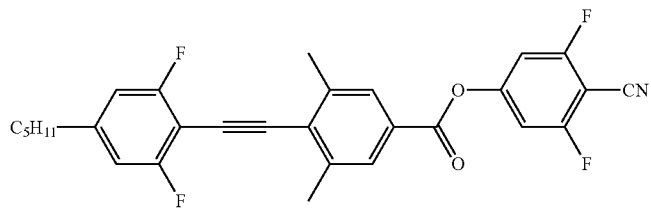 |
| 15 | 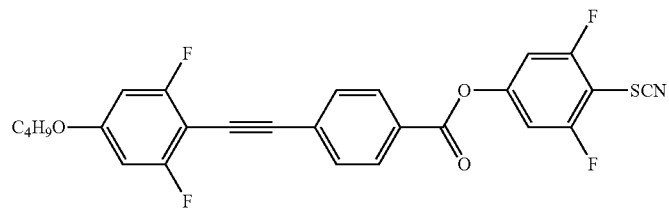 |
| 16 | 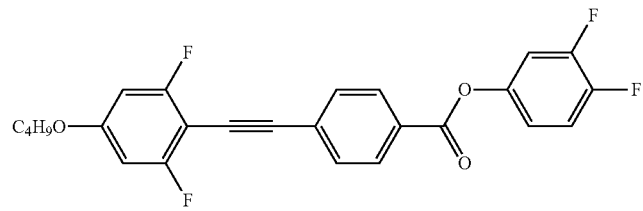 |
| 17 | 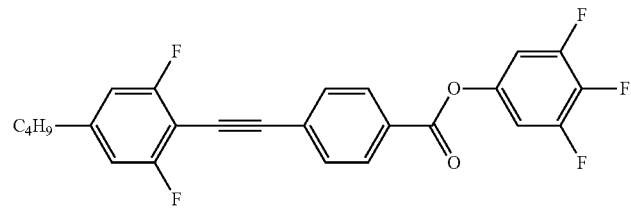 |
| 18 | 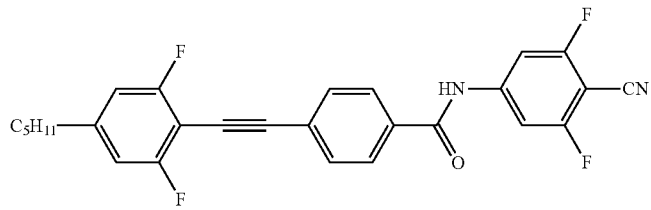 |
| 19 | 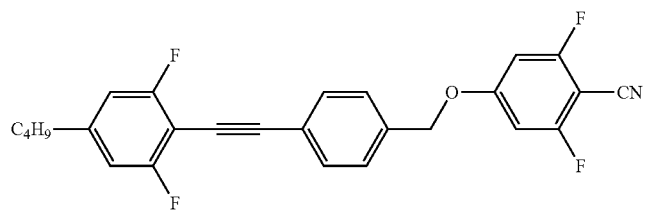 |

TABLE 1-continued

20
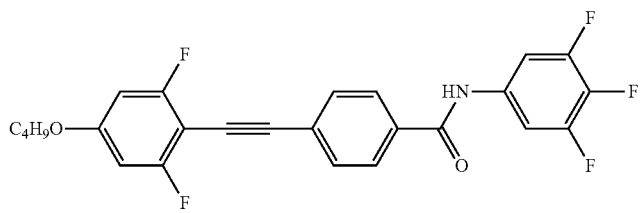

21
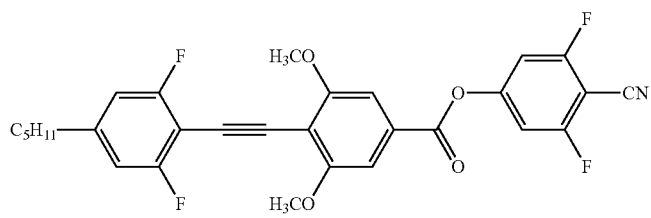

22
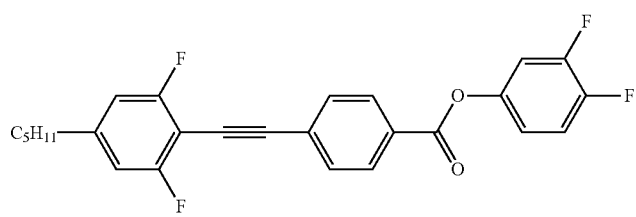

23
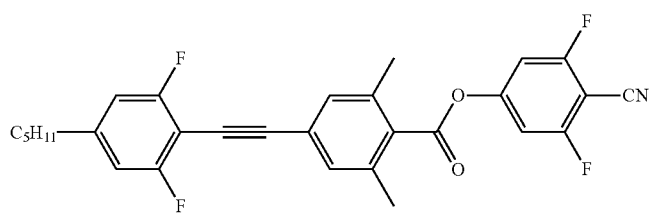

24
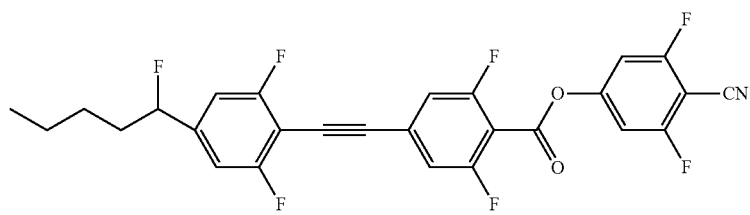 [SMILES: CCCCC(F)c1cc(F)c(C#Cc2cc(F)c(C(=O)Oc3cc(F)c(C#N)c(F)c3)c(F)c2)c(F)c1]

25
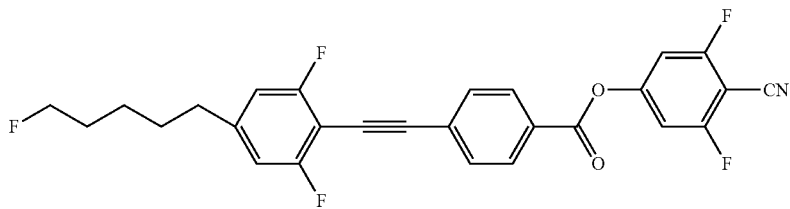 [SMILES: N#Cc1c(F)cc(OC(=O)c2ccc(C#Cc3c(F)cc(CCCCCF)cc3F)cc2)cc1F]

Experiments show that the liquid crystal compounds according to various embodiments of the disclosure have unexpectedly high dielectric anisotropy compared to well-known liquid crystal compounds, and therefore they can be used to decrease a driving voltage of a liquid crystal display.

The following formula (III) presents a known liquid crystal compound (referred to Germany Patent Application No. 10241721A1), wherein $R^1$ and $R^2$ may be $C_1$-$C_5$ alkyl, and $L_1$ may be fluorine. As show in formula (III), the liquid crystal compound has a fluorine substituted benzyl group and an alkyne group (as circled by the dotted line below), and the dielectric anisotropy of the liquid crystal compound is merely between 30 and 40. That is, the liquid crystal compound having a structure of formula (III) has a low dielectric anisotropy.

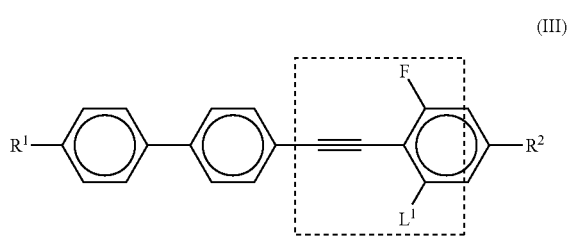

(III)

In addition, the following formula (IV) presents another known liquid crystal compound (referred to Taiwan Patent Application TW I314577), wherein $R^1$ and $R^2$ may be $C_1$-$C_{12}$ alkyl, and $A_1$, $A_2$, and $A_3$ may be halogen. As show in formula (IV), the liquid crystal compound has a benzyl group and —C(O)O— structure (as circled by the dotted line below), and the dielectric anisotropy of the liquid crystal compound is also merely between 30 and 40. That is, the liquid crystal compound having a structure of formula (IV) also has a low dielectric anisotropy.

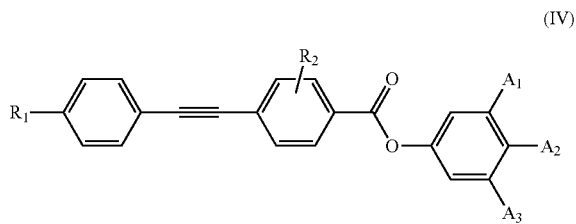

(IV)

That is, according to the results of the known liquid crystal compounds (III) and (IV), since both the liquid crystal compounds of formula (III) and formula (IV) have low diamagnetic anisotropies, it was originally held assumed that a structure with a fluorine substituted benzyl group and an alkyne group as shown in formula (III) and a structure with a benzyl group and —C(O)O— structure as shown in formula (IV) are structures that lead to low dielectric anisotropy.

However, experiments surprisingly showed that the liquid crystal compounds having a structure of formula (I) including a fluorine substituted benzyl group, an alkyne group, and a —C(O)O— structure have unexpectedly high dielectric anisotropy, for example, above 45. Therefore, the liquid crystal compounds having a structure of formula (I) can be used in a liquid crystal display to decrease the driving voltage of the display. In addition, when $X_1$ and/or $X_2$ in formula (II) is/are fluorine, the dielectric anisotropy may even reach 60. Thus, it can be used to decrease the driving voltage of the display substantially.

FIG. 1 is a cross-section view of a liquid crystal display according to one embodiment. Referring to FIG. 1, a liquid crystal display 100 includes a first substrate 102, a second substrate 104, and a liquid crystal layer 106, wherein the second substrate 104 is disposed opposite to the first substrate 102, and the liquid crystal layer 106 disposed between the first substrate 102 and the second substrate 104. The liquid crystal layer 106 further includes a liquid crystal monomer and the liquid crystal compound having a structure of formula (I), wherein the liquid crystal monomer is different from the liquid crystal compound, and the liquid crystal layer contains 5% to 15% by weight of the liquid crystal compound. In one embodiment, the liquid crystal display is an active liquid crystal display including arrays of a plurality of pixels, wherein each pixel may include a thin film transistor and a storage capacitor. In another embodiment, the liquid crystal display is a passive liquid crystal display, wherein a first electrode is disposed on the first substrate along a first direction and a second electrode is disposed on the second substrate along a second direction, perpendicular to the first direction. However, these structures of the liquid crystal displays are, of course, merely examples and are not intended to be limiting. Any well-known or future developed liquid crystal display structure can be used. For example, the liquid crystal display structures described in United States Patent Publication No. 20080122998 or No. 20110058136 can also be used.

Example 1

Synthesis of the Liquid Crystal Compound 1

1,3-difluoro-5-pentylbenzene (18.4 g; 100 mmol) and dried tetrahydrofuran (THF; 75 ml) were added into a reaction flask. After the 1,3-difluoro-5-pentylbenzene was dissolved, the solution was cooled to −78° C. When the temperature of the flask reached −78° C., n-butyllithium (66.4 ml; 110 mmol) was then added into the flask. The reaction continued under a low temperature for 1 hr, and the transparent liquid transferred into a white salt. Bromine (23.97 ml; 150 mmol) was then slowly added into the flask dropwise, and the reaction continued under a low temperature for 2 hrs. After 2 hrs, a temperature of the solution was raised back to room temperature, and the reaction was completed. After the reaction, ethyl acetate and water was used to extract the solution, and the resulting organic layer was concentrated under reduced pressure to obtain a brown liquid product. The reaction can be expressed by the following equation:

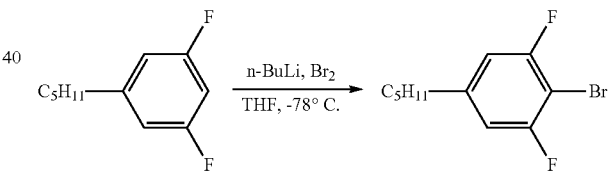

Next, the resulting brown product (17.68 g; 80 mmol) and dried triethylamine (60 ml) was added into a reaction flask under $N_2$ atmosphere. Then, bis(triphenylphosphine)palladium dichloride (Pd(PPh$_3$)$_2$Cl$_2$; 0.55 g; 0.8 mmol; yellow solid) and copper iodide (0.15 g; 0.8 mmol; white solid) were added into the flask and stirred for 0.5 hrs. Then, ethynyltrimethylsilane (22.4 ml; 160 mmol) was added dropwise into the flask. The solution was then heated to 77° C. and the reaction continued for 6 hrs. After the reaction, ethyl acetate and water were used to extract the product, and the resulting organic layer was concentrated under reduced pressure to obtain a brown product.

The resulting brown product (19.68 g; 75 mmol) was added into 100 ml of a solvent containing dichloromethane: methanol=1:1 and the resulting solution was stirred until the solid was dissolved. Then, $K_2CO_3$ (12.16 g; 88 mmol) was added into the solution and the resulting solution was stirred for 4 hrs. After the reaction, dichloromethane and water were used to extract the product, and a product of a yellow liquid in an organic layer was then obtained. The reaction can be expressed by the following equation:

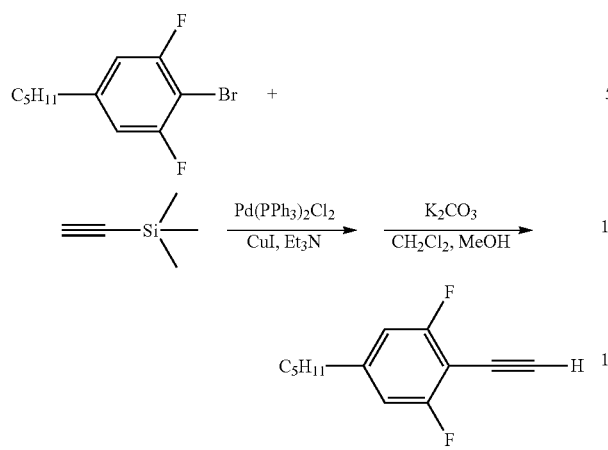

The resulting yellow liquid (17.12 g; 70 mmol), dried triethylamine (60 ml), and dried THF (60 ml) were added into a reaction flask under N$_2$ atmosphere. Bis(triphenylphosphine)palladium dichloride (0.51 g; 0.7 mmol) and copper iodide (0.14 g; 0.7 mmol) were then added into the flask, and the mixture was stirred for 0.5 hrs. Then, methyl 4-iodobenzoate (19.6 g; 75 mmol) was added into the solution and the resulting solution was heated to 70° C. The reaction continued for 12 hrs. After the reaction, ethyl acetate and water were used to extract the product, and the resulting organic layer was concentrated under reduced pressure to obtain a yellow solid product. The reaction can be expressed by the following equation:

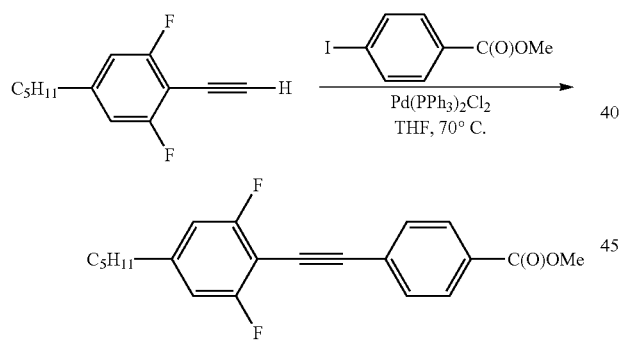

The resulting yellow product was then dissolved in a solution of water:ethanol=1:1 (60 ml), and NaOH (3.6 g; 150 mmol) was added into the solution. The solution was then heated to 60° C. The reaction was continued for 4 hrs. After the reaction, ethyl acetate and water were used to extract the product, and the resulting organic layer was concentrated under reduced pressure to obtain a white solid product. The reaction can be expressed by the following equation:

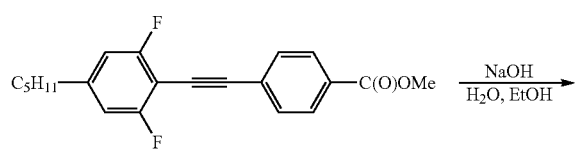

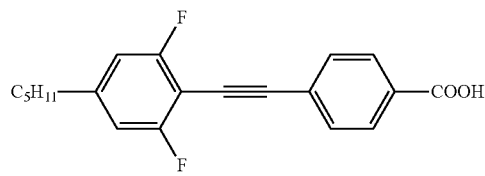

The resulting white product (19.7 g; 60 mmol) and dried THF (50 ml) were added into a reaction flask under N$_2$ atmosphere. Then, 3,4,5,-trifluorophenol, as a white solid, (8.8 g; 60 mmol), 4-(dimethylamino) pyridine (DMPA; 2.9 g; 24 mmol), and dicyclohexylcarbodiimide (DCC; 14.8 g; 72 mmol) were added into the solution. The solution was then heated to 70° C. The reaction was continued for 6 hrs. After the reaction, ethyl acetate and water were used to extract the product, and the resulting organic layer was concentrated under reduced pressure. A yellow solid product was then obtained as a crude product. The crude product was recrystallized twice by hexane and dichloromethane to obtain a liquid crystal compound 1 as a white solid (19.7 g; 43 mmol; yield: 43%). The reaction can be expressed by the following equation:

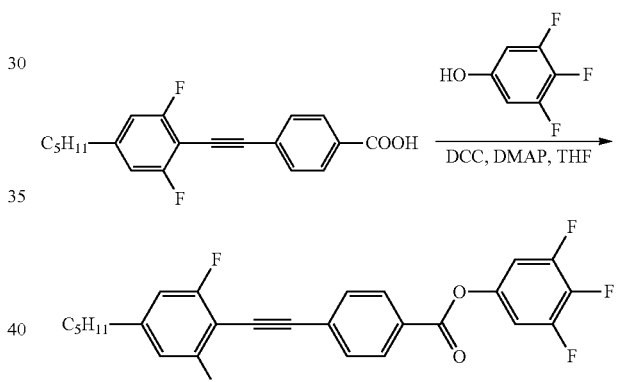

Example 2

Synthesis of the Liquid Crystal Compound 2

1,3-difluoro-5-pentylbenzene (18.4 g; 100 mmol) and dried tetrahydrofuran (THF; 75 ml) were added into a reaction flask. After the 1,3-difluoro-5-pentylbenzene was dissolved, the solution was cooled to −78° C. When the temperature of the solution reached −78° C., n-butyllithium (66.4 ml; 110 mmol) was then added into the flask. The reaction continued under a low temperature for 1 hr, and the transparent liquid transferred into a white salt. Bromine (23.97 ml; 150 mmol) was then slowly added into the flask dropwise, and the reaction continued under a low temperature for 2 hrs. After 2 hrs, a temperature of the solution was put back to room temperature, and the reaction was completed. After the reaction, ethyl acetate and water was used to extract the product, and the resulting organic layer was concentrated under reduced pressure to obtain a brown liquid product. The reaction can be expressed by the following equation:

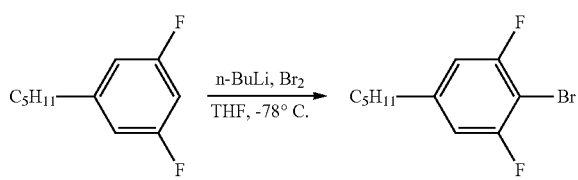

Next, the resulting brown product (17.68 g; 80 mmol) and dried triethylamine (60 ml) was added into a reaction flask under $N_2$ atmosphere. Then, bis(triphenylphosphine)palladium dichloride ($Pd(PPh_3)_2Cl_2$; 0.55 g; 0.8 mmol) and copper iodide (0.15 g; 0.8 mmol) were added into the flask and stirred for 0.5 hrs. Then, ethynyltrimethylsilane (22.4 ml; 160 mmol) was added dropwise into the flask. The solution was then heated to 77° C. and the reaction continued for 6 hrs. After the reaction, ethyl acetate and water were used to extract the product, and the resulting organic layer was concentrated under reduced pressure to obtain a brown product.

The resulting brown product (19.68 g; 75 mmol) was added into 100 ml of a solvent containing dichloromethane:methanol=1:1 and the resulting solution was stirred until the solid was dissolved. Then, $K_2CO_3$ (12.16 g; 88 mmol) was added into the solution and the resulting solution was stirred for 4 hrs. After the reaction, dichloromethane and water were used to extract the product, and a product of a yellow liquid was then obtained in the organic layer. The reaction can be expressed by the following equation:

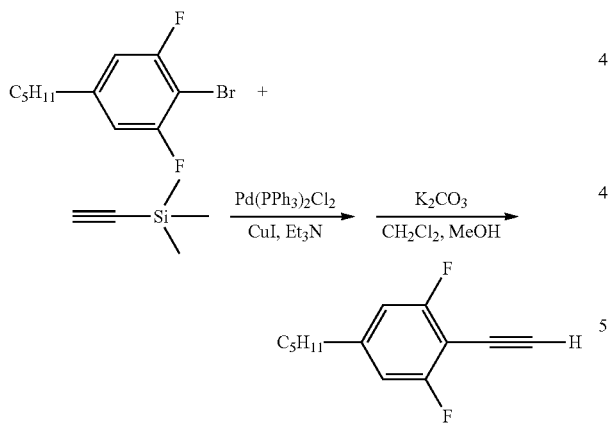

The resulting yellow liquid (17.12 g; 70 mmol), dried triethylamine (60 ml), and dried THF (60 ml) were added into a reaction flask under $N_2$ atmosphere. Bis(triphenylphosphine)palladium dichloride (0.51 g; 0.7 mmol) and copper iodide (white solid; 0.14 g; 0.7 mmol) were then added into the flask, and the mixture was stirred for 0.5 hrs. Then, methyl 4-iodobenzoate (19.6 g; 75 mmol) was added into the solution and the resulting solution was heated to 70° C. The reaction was continued for 12 hrs. After the reaction, ethyl acetate and water were used to extract the product, and the resulting organic layer was concentrated under reduced pressure to obtain a yellow solid product. The reaction can be expressed by the following equation:

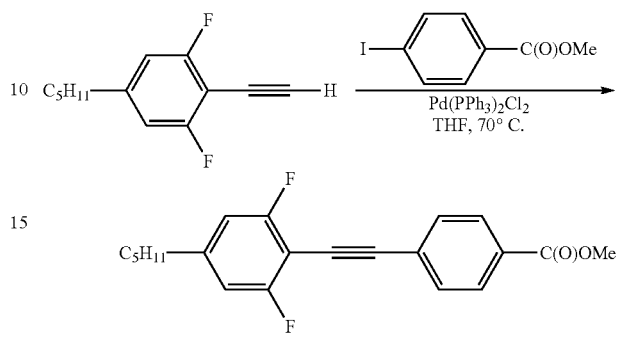

The resulting yellow product was then dissolved in a solution of water:ethanol=1:1 (60 ml), and NaOH (3.6 g; 150 mmol) was added into the solution. The solution was then heated to 60° C. The reaction was continued for 4 hrs. After the reaction, ethyl acetate and water were used to extract the product, and the resulting organic layer was concentrated under reduced pressure to obtain a white solid product. The reaction can be expressed by the following equation:

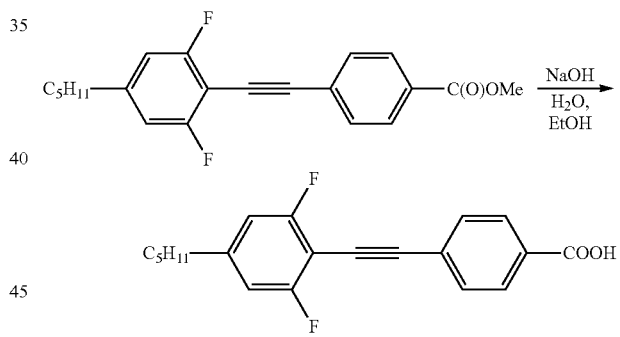

The resulting white product (19.7 g; 60 mmol) and dried THF (50 ml) were added into a flask. After the white product was dissolved, 4-cyano-3,5-difluorophenol (9.3 g; 60 mmol), 4-(dimethylamino) pyridine (DMPA; 2.9 g; 24 mmol), and dicyclohexylcarbodiimide (DCC; 14.8 g; 72 mmol) were added into the solution under $N_2$ atmosphere. The solution was then heated to 70° C. The reaction was continued for 6 hrs. After the reaction, ethyl acetate and water were used to extract the product, and the resulting organic layer was concentrated under reduced pressure. A yellow solid product was then obtained as a crude product. The crude product was recrystallized twice by hexane and dichloromethane to obtain the liquid crystal compound 2 as a white solid (20.9 g; 45 mmol; yield: 45%). The reaction can be expressed by the following equation:

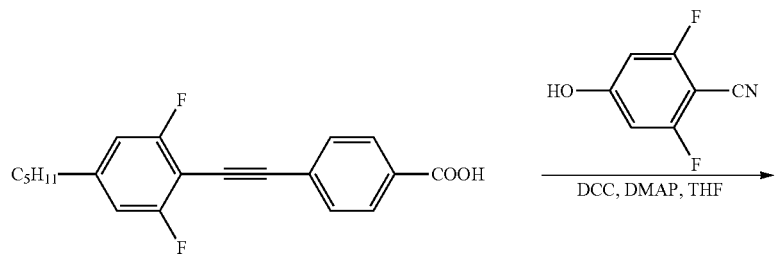

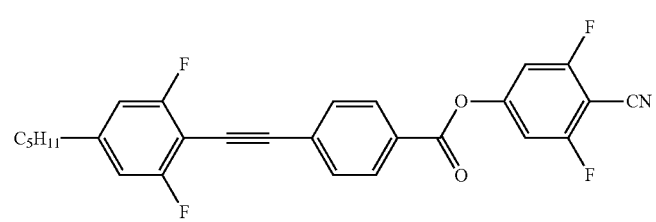

Example 3

Synthesis of the Liquid Crystal Compound 3

3,5-difluorophenol (14.3 g; 110 mmol), $K_2CO_3$ (22.80 g; 165 mmol), and acetone (100 ml) were added into a reaction flask. 1-bromobutane (15.1 ml; 110 mmol) was added into the flask dropwise. The solution was heated to 60° C. and the reaction continued for 6 hrs. After the reaction, ethyl acetate and water was used to extract the product, and the resulting organic layer was concentrated under reduced pressure to obtain a white liquid product. The reaction can be expressed by the following equation:

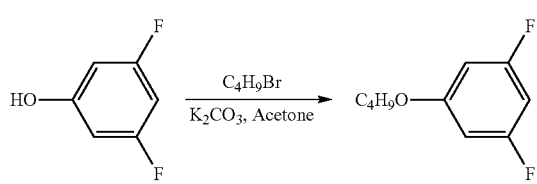

The resulting white liquid (18.4 g; 100 mmol) and dried tetrahydrofuran (THF; 75 ml) were added into a reaction flask. Then, the solution was cooled to −78° C. When the temperature of the solution reached −78° C., n-butyllithium (66.4 ml; 110 mmol) was then added into the flask. The reaction continued under a low temperature for 1 hr, and the transparent liquid transferred into a white salt. Bromine (23.97 ml; 150 mmol) was then slowly added into the flask dropwise, and the reaction continued under a low temperature for 2 hrs. After 2 hrs, a temperature of the solution was raised back to room temperature, and the reaction was completed. After the reaction, ethyl acetate and water was used to extract the product, and the resulting organic layer was concentrated under reduced pressure to obtain a brown liquid product. The reaction can be expressed by the following equation:

Next, the resulting brown product (17.68 g; 80 mmol) and dried triethylamine (60 ml) was added into a reaction flask under $N_2$ atmosphere. Then, bis(triphenylphosphine)palladium dichloride (0.55 g; 0.8 mmol) and copper iodide (0.15 g; 0.8 mmol) were added into the flask and stirred for 0.5 hrs. Then, ethynyltrimethylsilane (22.4 ml; 160 mmol) was added dropwise into the flask. The solution was then heated to 77° C. and the reaction continued for 6 hrs. After the reaction, ethyl acetate and water were used to extract the product, and the resulting organic layer was concentrated under reduced pressure to obtain a brown product.

The resulting brown product (19.68 g; 75 mmol) was added into 100 ml of a solvent containing dichloromethane: methanol=1:1 and the resulting solution was stirred until the solid was dissolved. Then, $K_2CO_3$ (12.16 g; 88 mmol) was added into the solution and the resulting solution was stirred for 4 hrs. After the reaction, dichloromethane and water were used to extract the product, and a product of a yellow liquid in an organic layer was then obtained. The reaction can be expressed by the following equation:

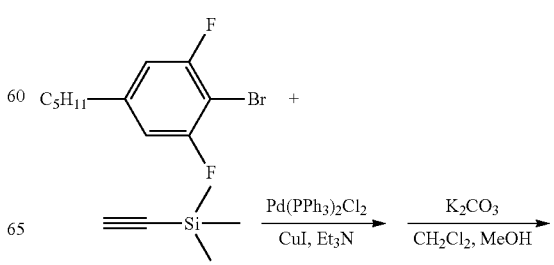

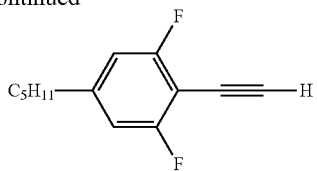

The resulting yellow liquid (17.12 g; 70 mmol), dried triethylamine (60 ml), and dried THF (60 ml) were added into a reaction flask under N₂ atmosphere. Bis(triphenylphosphine)palladium dichloride (0.51 g; 0.7 mmol) and copper iodide (white solid; 0.14 g; 0.7 mmol) were then added into the flask, and the mixture was stirred for 0.5 hrs. Then, methyl 4-iodobenzoate (19.6 g; 75 mmol) was added into the flask and the resulting solution was heated to 70° C. The reaction continued for 12 hrs. After the reaction, ethyl acetate and water were used to extract the product, and the resulting organic layer was concentrated under reduced pressure to obtain a yellow solid product. The reaction can be expressed by the following equation:

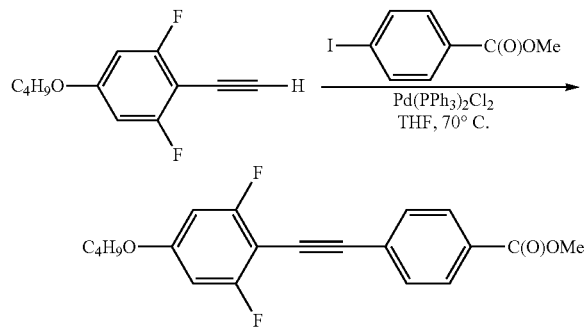

The resulting yellow product was then dissolved in a solution of water:ethanol=1:1 (60 ml), and NaOH (3.6 g; 150 mmol) was added into the solution. The solution was then heated to 60° C. The reaction was continued for 4 hrs. After the reaction, ethyl acetate and water were used to extract the product, and the resulting organic layer was concentrated under reduced pressure to obtain a white solid product. The reaction can be expressed by the following equation:

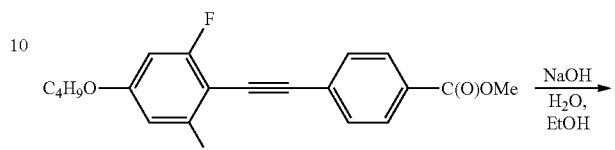

The resulting white product (19.7 g; 60 mmol) and dried THF (54-cyano-3,5-difluorophenol 3,4,5,-trifluorophenol (9.3 g; 60 mmol), 4-(dimethylamino) pyridine (DMPA; 2.9 g; 24 mmol), and dicyclohexylcarbodiimide (DCC; 14.8 g; 72 mmol) were added into the solution. The solution was then heated to 70° C. The reaction was continued for 6 hrs. After the reaction, ethyl acetate and water were used to extract the product, and the resulting organic layer was concentrated under reduced pressure. A yellow solid product was then obtained as a crude product. The crude product was recrystallized twice by hexane and dichloromethane to obtain a liquid crystal compound 3 as a light yellow solid (22.9 g; 49 mmol; yield: 44%). The reaction can be expressed by the following equation:

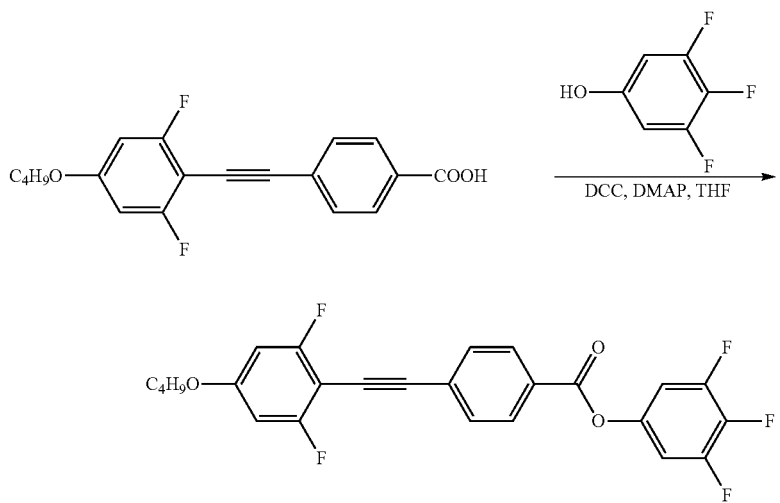

Example 4

Synthesis of the Liquid Crystal Compound 4

1,3-difluoro-5-pentylbenzene (18.4 g; 100 mmol) and dried tetrahydrofuran (THF; 75 ml) were added into a reaction flask. After the 1,3-difluoro-5-pentylbenzene was dissolved, the solution was cooled to −78° C. When the temperature of the solution reached −78° C., n-butyllithium (66.4 ml; 110 mmol) was then added into the flask. The reaction continued under a low temperature for 1 hr, and the transparent liquid transferred into a white salt. Bromine (23.97 ml; 150 mmol) was then slowly added into the flask dropwise, and the reaction continued under a low temperature for 2 hrs. After 2 hrs, a temperature of the solution was put back to room temperature, and the reaction was completed. After the reaction, ethyl acetate and water was used to extract the product, and the resulting organic layer was concentrated under reduced pressure to obtain a brown liquid product. The reaction can be expressed by the following equation:

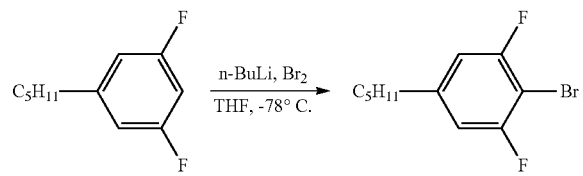

Next, the resulting brown product (17.68 g; 80 mmol) and dried triethylamine (60 ml) was added into a reaction flask under $N_2$ atmosphere. Then, bis(triphenylphosphine)palladium dichloride ($Pd(PPh_3)_2Cl_2$; 0.55 g; 0.8 mmol) and copper iodide (0.15 g; 0.8 mmol) were added into the flask and stirred for 0.5 hrs. Then, ethynyltrimethylsilane (22.4 ml; 160 mmol) was added dropwise into the flask. The solution was then heated to 77° C. and the reaction continued for 6 hrs. After the reaction, ethyl acetate and water were used to extract the product, and the resulting organic layer was concentrated under reduced pressure to obtain a brown product.

The resulting brown product (19.68 g; 75 mmol) was added into 100 ml of a solvent containing dichloromethane: methanol=1:1 and the resulting solution was stirred until the solid was dissolved. Then, $K_2CO_3$ (12.16 g; 88 mmol) was added into the solution and the resulting solution was stirred for 4 hrs. After the reaction, dichloromethane and water were used to extract the product, and a product of a yellow liquid in an organic layer was then obtained. The reaction can be expressed by the following equation:

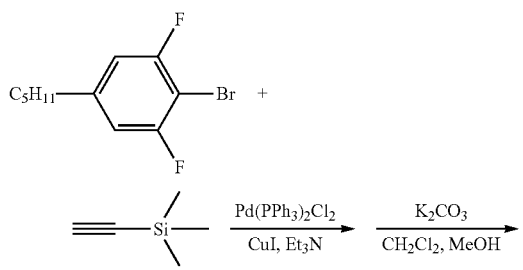

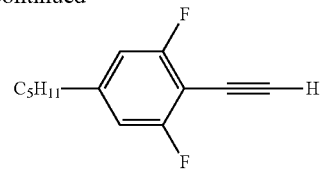

The resulting yellow liquid (17.12 g; 70 mmol), dried triethylamine (60 ml), and dried THF (60 ml) were added into a reaction flask under $N_2$ atmosphere. Bis(triphenylphosphine)palladium dichloride (0.51 g; 0.7 mmol) and copper iodide (0.14 g; 0.7 mmol) were then added into the flask, and the mixture was stirred for 0.5 hrs. Then, methyl 4-iodobenzoate (19.6 g; 75 mmol) was added into the flask and the resulting solution was heated to 70° C. The reaction continued for 12 hrs. After the reaction, ethyl acetate and water were used to extract the product, and the resulting organic layer was concentrated under reduced pressure to obtain a yellow solid product. The reaction can be expressed by the following equation:

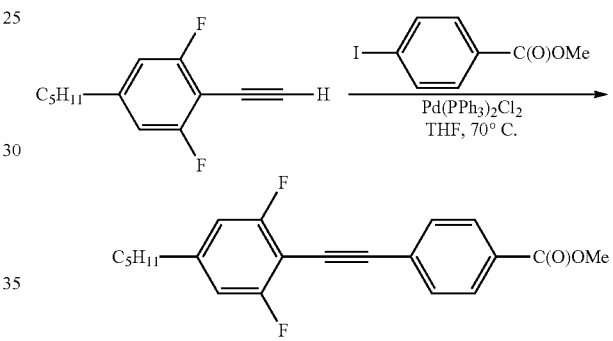

The resulting yellow product was then dissolved in a solution of water:ethanol=1:1 (60 ml), and NaOH (3.6 g; 150 mmol) was added into the solution. The solution was then heated to 60° C. The reaction was continued for 4 hrs. After the reaction, ethyl acetate and water were used to extract the product, and the resulting organic layer was concentrated under reduced pressure to obtain a white solid product. The reaction can be expressed by the following equation:

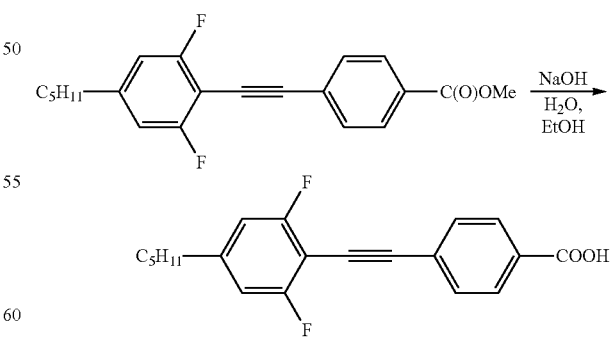

The resulting white product (19.7 g; 60 mmol) and dried THF (50 ml) were added into a flask. After the white product was dissolved, 3,4,5,-trifluorophenol, as a white solid, (9.3 g; 60 mmol), 4-(dimethylamino) pyridine (DMPA; 2.9 g; 24 mmol), and dicyclohexylcarbodiimide (DCC; 14.8 g; 72 mmol) were added into the solution under $N_2$ atmosphere. The solution was then heated to 70° C. The reaction continued for 6 hrs. After the reaction, ethyl acetate and water were used to extract the product, and the resulting organic layer was concentrated under reduced pressure. A yellow solid product was then obtained as a crude product. The crude product was recrystallized twice by hexane and dichloromethane to obtain a liquid crystal compound 17 as a white solid (20.1 g; 44 mmol; yield: 44%). The reaction can be expressed by the following equation:

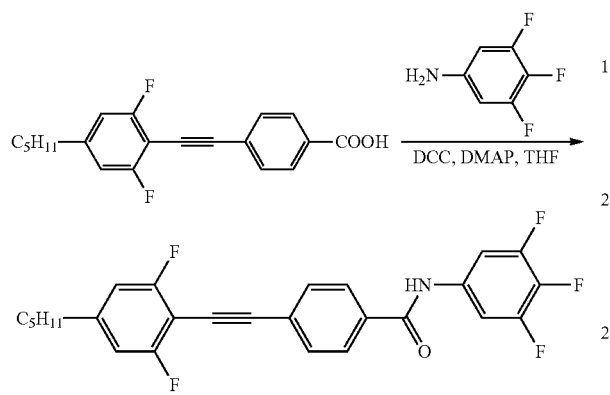

Example 5

Synthesis of the Liquid Crystal Compound 5

1,3-difluoro-5-pentylbenzene (18.4 g; 100 mmol) and dried tetrahydrofuran (THF; 75 ml) were added into a reaction flask. After the 1,3-difluoro-5-pentylbenzene was dissolved, the solution was cooled to −78° C. When the temperature of the flask reached −78° C., n-butyllithium (66.4 ml; 110 mmol) was then added into the flask. The reaction continued under a low temperature for 1 hr, and the transparent liquid transferred into a white salt. Bromine (23.97 ml; 150 mmol) was then slowly added into the flask dropwise, and the reaction continued under a low temperature for 2 hrs. After 2 hrs, a temperature of the solution was raised back to room temperature, and the reaction was completed. After the reaction, ethyl acetate and water was used to extract the solution, and the resulting organic layer was concentrated under reduced pressure to obtain a brown liquid product. The reaction can be expressed by the following equation:

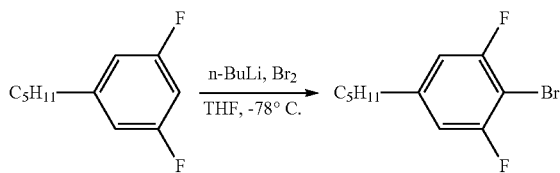

Next, the resulting brown product (17.68 g; 80 mmol) and dried triethylamine (60 ml) was added into a reaction flask under $N_2$ atmosphere. Then, bis(triphenylphosphine)palladium dichloride ($Pd(PPh_3)_2Cl_2$; 0.55 g; 0.8 mmol; yellow solid) and copper iodide (0.15 g; 0.8 mmol; white solid) were added into the flask and stirred for 0.5 hrs. Then, ethynyltrimethylsilane (22.4 ml; 160 mmol) was added dropwise into the flask. The solution was then heated to 77° C. and the reaction continued for 6 hrs. After the reaction, ethyl acetate and water were used to extract the product, and the resulting organic layer was concentrated under reduced pressure to obtain a brown product.

The resulting brown product (19.68 g; 75 mmol) was added into 100 ml of a solvent containing dichloromethane: methanol=1:1 and the resulting solution was stirred until the solid was dissolved. Then, $K_2CO_3$ (12.16 g; 88 mmol) was added into the solution and the resulting solution was stirred for 4 hrs. After the reaction, dichloromethane and water were used to extract the product, and a product of a yellow liquid in an organic layer was then obtained. The reaction can be expressed by the following equation Part A:

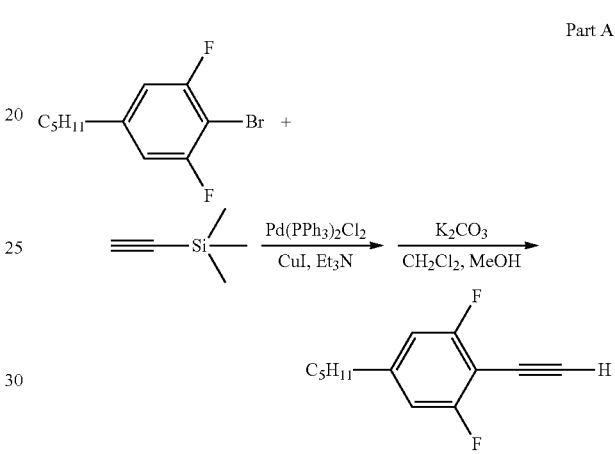

3,5-difluorophenol (14.2 g; 60 mmol) was added into a reaction flask. 50 ml of thionyl chloride ($SOCl_2$) was added into the flask and heated to 75° C. The reaction continued for 2 hrs, such that all of the solid was dissolved. After the reaction, thionyl chloride was removed by reduced pressure distillation to obtain a brown liquid intermediate product. 3,4,5-trifluorophenol (9.3 g; 60 mmol) was added into a second reaction flask and was dissolved in 50 ml of pyridine. The brown liquid intermediate product was added into the second reaction flask dropwise. The mixture was heated to 70° C. and the reaction was continued over night.

On the next day, the mixture was cooled down to room temperature, and a great amount of water was added into the mixture to obtain an esterified white product B. Pyridine and water were removed by an air suction filter. The resulting product was dried in a vacuum oven at 70° C. until the next day. The reaction can be expressed by the following equation Part B:

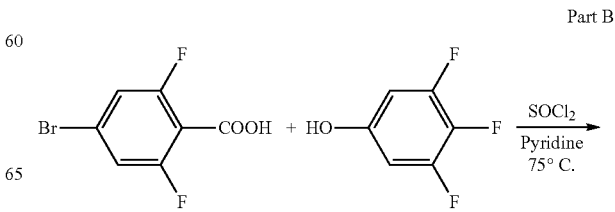

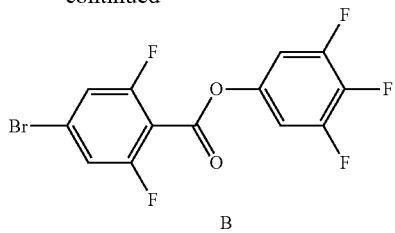

B

Solid catalyst, bis(triphenylphosphine)palladium dichloride($Pd(PPh_3)_2Cl_2$) (1.75 g, 2 mol %), copper iodide (CuI; 0.5 g; 2 mol %), and triphenylphosphine ($PPh_3$; 1.3 g; 4 mol %) were put into a reaction flask. The reaction flask was vacuumized and then a nitrogen flow was pump in. Next, dried triethylamine was added into the flask, and then the product B (obtained by formula Part B; 18.3 g; 50 mmol) was also added into the flask. After stirring the flask, product A (obtained by formula Part A; 10.4 g; 50 mmol) was added into the flask, and then the flask was heated to 75° C. in darkness. The reaction was continued overnight. After the reaction, the mixture was cooled down to room temperature and concentrated under reduced pressure. After that, 22.7 g of a white solid product was obtained (46 mmol) with a yield of 46%. The reaction can be expressed by the following equation Part C:

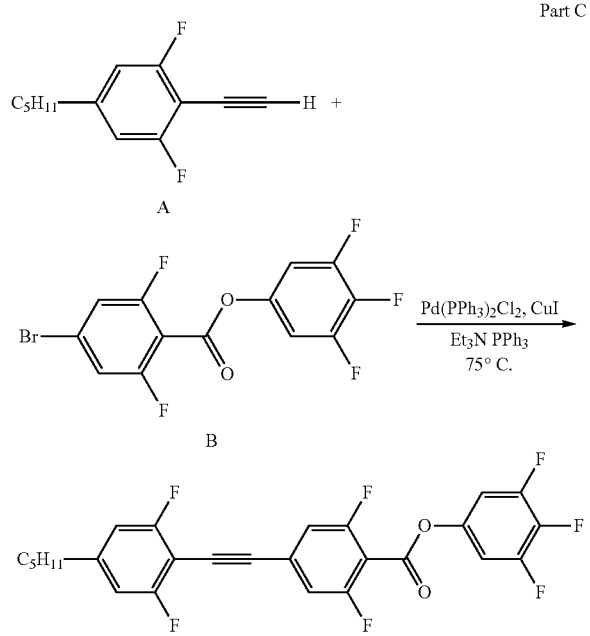

Example 6

Synthesis of the Liquid Crystal Compound 6

1,3-difluoro-5-pentylbenzene (18.4 g; 100 mmol) and dried tetrahydrofuran (THF; 75 ml) were added into a reaction flask. After the 1,3-difluoro-5-pentylbenzene was dissolved, the solution was cooled to −78° C. When the temperature of the flask reached −78° C., n-butyllithium (66.4 ml; 110 mmol) was then added into the flask. The reaction continued under a low temperature for 1 hr, and the transparent liquid transferred into a white salt. Bromine (23.97 ml; 150 mmol) was then slowly added into the flask dropwise, and the reaction continued under a low temperature for 2 hrs. After 2 hrs, a temperature of the solution was raised back to room temperature, and the reaction was completed. After the reaction, ethyl acetate and water was used to extract the solution, and the resulting organic layer was concentrated under reduced pressure to obtain a brown liquid product. The reaction can be expressed by the following equation:

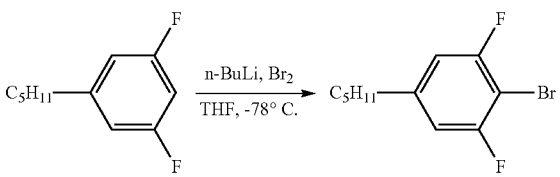

Next, the resulting brown product (17.68 g; 80 mmol) and dried triethylamine (60 ml) was added into a reaction flask under $N_2$ atmosphere. Then, bis(triphenylphosphine)palladium dichloride ($Pd(PPh_3)_2Cl_2$; 0.55 g; 0.8 mmol; yellow solid) and copper iodide (0.15 g; 0.8 mmol; white solid) were added into the flask and stirred for 0.5 hrs. Then, ethynyltrimethylsilane (22.4 ml; 160 mmol) was added dropwise into the flask. The solution was then heated to 77° C. and the reaction continued for 6 hrs. After the reaction, ethyl acetate and water were used to extract the product, and the resulting organic layer was concentrated under reduced pressure to obtain a brown product.

The resulting brown product (19.68 g; 75 mmol) was added into 100 ml of a solvent containing dichloromethane:methanol=1:1 and the resulting solution was stirred until the solid was dissolved. Then, $K_2CO_3$ (12.16 g; 88 mmol) was added into the solution and the resulting solution was stirred for 4 hrs. After the reaction, dichloromethane and water were used to extract the product, and a product of a yellow liquid in an organic layer was then obtained. The reaction can be expressed by the following equation Part A:

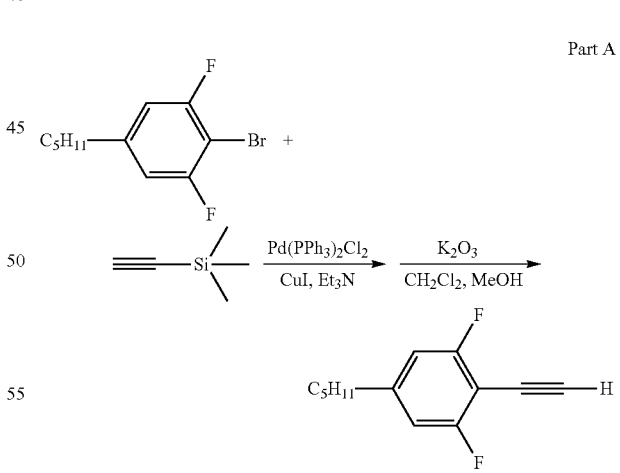

3,5-difluoro-4-bromobenzonic acid (14.22 g; 60 mmol) was added into a reaction flask. 50 ml of thionyl chloride ($SOCl_2$) was added into the flask and heated to 75° C. The reaction continued for 2 hrs, such that all of the solid was dissolved. After the reaction, thionyl chloride was removed by reduced pressure distillation to obtain a brown liquid intermediate product. 3,5-difluorophenol (7.8 g; 60 mmol) was added into a second reaction flask and was dissolved in 50 ml of pyridine. The brown liquid intermediate product was added into the second reaction flask dropwise. The mixture was heated to 70° C. and the reaction was continued over night.

On the next day, the mixture was cooled down to room temperature, and a great amount of water was added into the mixture to obtain an esterified white product B. Pyridine and water were removed by an air suction filter. The resulting product was dried in a vacuum oven at 70° C. until the next day. The reaction can be expressed by the following equation Part B:

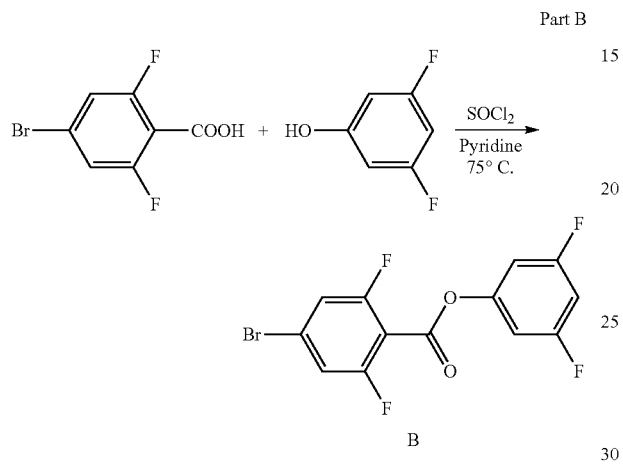

Solid catalyst, bis(triphenylphosphine)palladium dichloride(Pd(PPh$_3$)$_2$Cl$_2$) (1.7 g, 2 mol %), copper iodide (CuI; 0.5 g; 2 mol %), and triphenylphosphine (PPh$_3$; 1.3 g; 4 mol %) were put into a reaction flask. The reaction flask was vacuumized and then a nitrogen flow was pump in. Next, dried triethylamine was added into the flask, and then the product B (obtained by formula Part B; 18.3 g; 50 mmol) was also added into the flask. After stirring the flask, product A (obtained by formula Part A; 10.4 g; 50 mmol) was added into the flask, and then the flask was heated to 75° C. in darkness. The reaction was continued overnight. After the reaction, the mixture was cooled down to room temperature and concentrated under reduced pressure. After that, 19.5 g of white solid product was obtained (41 mmol) with a yield of 41%. The reaction can be expressed by the following equation Part C:

Example 7

Synthesis of the Liquid Crystal Compound 22

1,3-difluoro-5-pentylbenzene (18.4 g; 100 mmol) and dried tetrahydrofuran (THF; 75 ml) were added into a reaction flask. After the 1,3-difluoro-5-pentylbenzene was dissolved, the solution was cooled to −78° C. When the temperature of the flask reached −78° C., n-butyllithium (66.4 ml; 110 mmol) was then added into the flask. The reaction continued under a low temperature for 1 hr, and the transparent liquid transferred into a white salt. Bromine (23.97 ml; 150 mmol) was then slowly added into the flask dropwise, and the reaction continued under a low temperature for 2 hrs. After 2 hrs, a temperature of the solution was raised back to room temperature, and the reaction was completed. After the reaction, ethyl acetate and water was used to extract the solution, and the resulting organic layer was concentrated under reduced pressure to obtain a brown liquid product. The reaction can be expressed by the following equation:

Next, the resulting brown product (17.68 g; 80 mmol) and dried triethylamine (60 ml) was added into a reaction flask under N$_2$ atmosphere. Then, bis(triphenylphosphine)palladium dichloride (Pd(PPh$_3$)$_2$Cl$_2$; 0.55 g; 0.8 mmol; yellow solid) and copper iodide (0.15 g; 0.8 mmol; white solid) were added into the flask and stirred for 0.5 hrs. Then, ethynyltrimethylsilane (22.4 ml; 160 mmol) was added dropwise into the flask. The solution was then heated to 77° C. and the reaction continued for 6 hrs. After the reaction, ethyl acetate and water were used to extract the product, and the resulting organic layer was concentrated under reduced pressure to obtain a brown product.

The resulting brown product (19.68 g; 75 mmol) was added into 100 ml of a solvent containing dichloromethane: methanol=1:1 and the resulting solution was stirred until the solid was dissolved. Then, K$_2$CO$_3$ (12.16 g; 88 mmol) was added into the solution and the resulting solution was stirred for 4 hrs. After the reaction, dichloromethane and water were used to extract the product, and a product of a yellow liquid in an organic layer was then obtained. The reaction can be expressed by the following equation Part A:

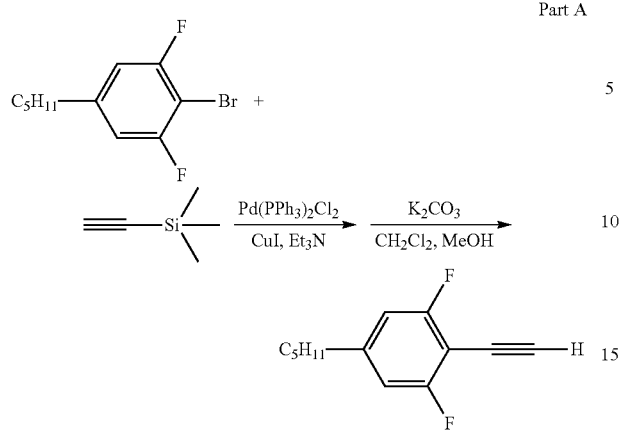

Part A 3,5-difluoro-4-bromobenzoic acid (14.22 g; 60 mmol) was added into a reaction flask. 50 ml of thionyl chloride (SOCl$_2$) was added into the flask and heated to 75° C. The reaction was continued for 2 hrs, such that all the solid had been dissolved. After the reaction, thionyl chloride was removed by reduced pressure distillation to obtain a brown liquid intermediate product. 2,6-difluoro-4-hydroxybenzonitrile (9.3 g; 60 mmol) was added into a second reaction flask and was dissolved in 50 ml of pyridine. The brown liquid intermediate product was added into the second reaction flask dropwise. The mixture was heated to 70° C. and the reaction was continued over night.

On the next day, the mixture was cooled down to room temperature, and a great amount of water was added into the mixture to obtain an esterified white product B. Pyridine and water were removed by an air suction filter. The resulting product was dried in a vacuum oven at 70° C. until the next day. The reaction can be expressed by the following equation Part B:

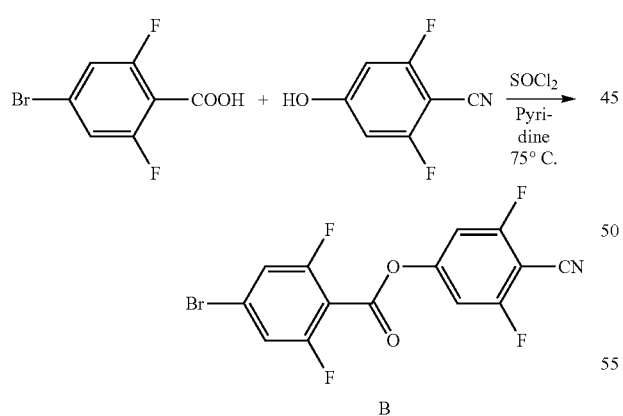

Part B

Solid catalyst, bis(triphenylphosphine)palladium dichloride(Pd(PPh$_3$)$_2$Cl$_2$) (1.75 g, 2 mol %), copper iodide (CuI; 0.5 g; 2 mol %), and triphenylphosphine (PPh$_3$; 1.3 g; 4 mol %) were put into a reaction flask. The reaction flask was vacuumized and then a nitrogen flow was pump in. Next, dried triethylamine was added into the flask, and then the product B (obtained by formula Part B; 18.3 g; 50 mmol) was also added into the flask. After stirring the flask, product A (obtained by formula Part A; 10.4 g; 50 mmol) was added into the flask, and then the flask was heated to 75° C. in darkness. The reaction was continued overnight. After the reaction, the mixture was cooled down to room temperature and concentrated under reduced pressure. After that, 22.7 g of a white solid product was obtained (46 mmol) with a yield of 46%. The reaction can be expressed by the following equation Part C:

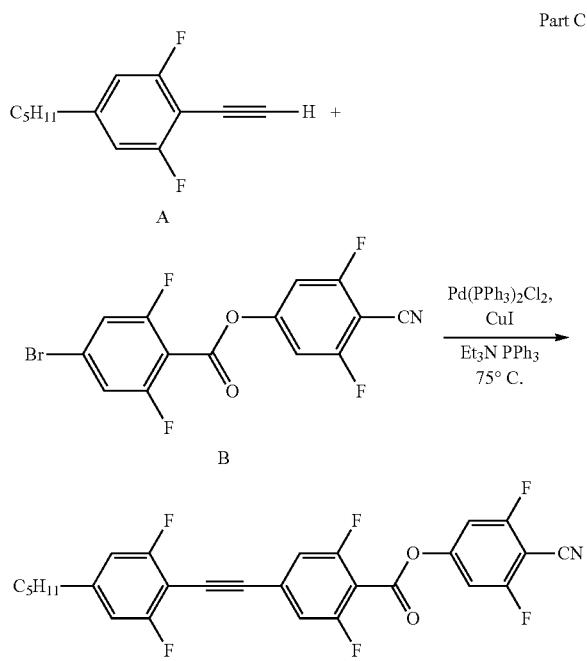

Part C

Comparative Example 1

A commercial liquid crystal compound having following formula (purchased from Merck; PPTUI-3-2) was used as the Comparative Example 1.

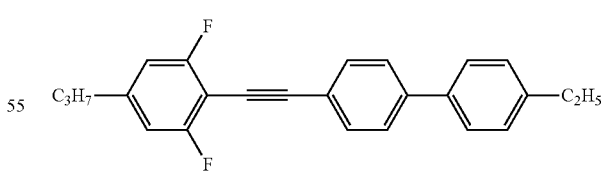

Comparative Example 2

4-Iodobenzoic acid (24.8 g; 100 mmol) and dried THF (60 ml) were added into a flask, and the 4-Iodobenzoic acid was dissolved. Under N₂ atmosphere, 3,4-difluorophenol (14.6 g; 60 mmol), 4-(dimethylamino) pyridine (14.6 g; 60 mmol), and dicyclohexylcarbodiimide (24.6 g; 120 mmol) were also added into the flask. The solution was heated to 70° C., and the reaction continued for 6 hrs. After the reaction, ethyl acetate and water were used to extract the product, and the resulting organic layer was concentrated under reduced pressure to obtain a yellow solid product. The reaction can be expressed by the following equation:

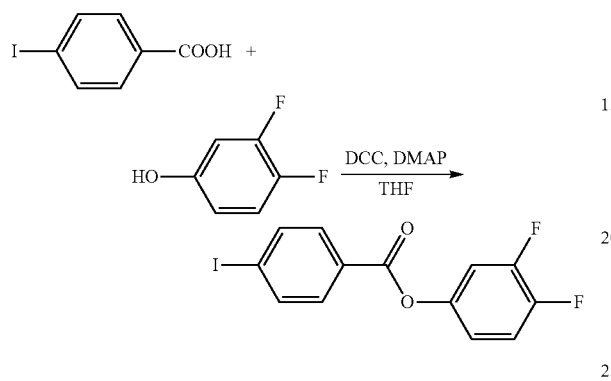

Next, the resulting yellow product (32.13 g; 85 mmol), dried triethylamine (60 ml), and dried THF (60 ml) were added into a reaction flask under N₂ atmosphere. Then, bis(triphenylphosphine)palladium dichloride used as a catalyst (0.51 g; 0.7 mmol) and copper iodide (0.18 g; 0.7 mmol) were added into the flask and stirred for 0.5 hrs. Then, methyl 4-iodobenzoate (15.49 g; 90 mmol) was then added into the mixture. The solution was then heated to 70° C. and the reaction continued for 12 hrs. After the reaction, ethyl acetate and water were used to extract the product, and the resulting organic layer was concentrated under reduced pressure. A yellow solid was then obtained as a crude product. The crude product was recrystallized twice by hexane and dichloromethane to obtain a white solid (28.3 g; 67 mmol; yield: 67%). The reaction can be expressed by the following equation:

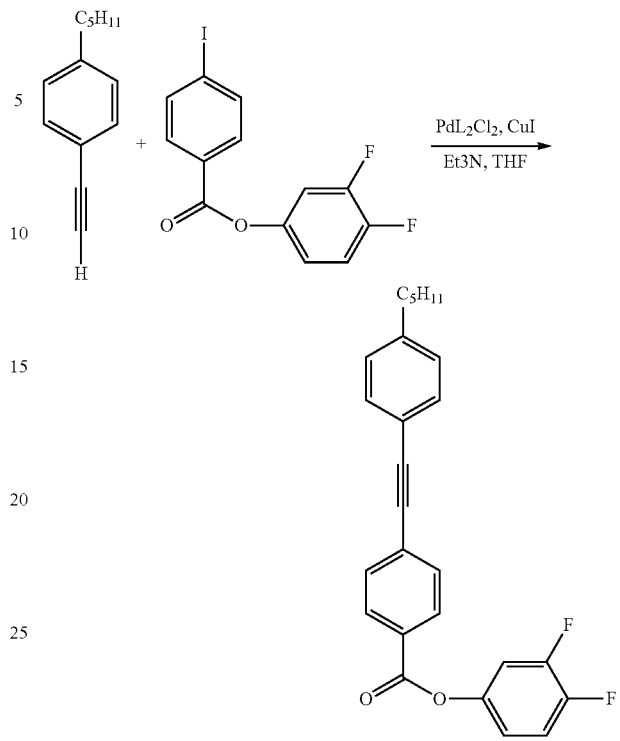

Example 8

Dielectric Anisotropy of Liquid Crystal Compounds

The liquid crystal compounds in Example 1 to 4 were added into a passive matrix (PM) liquid crystal formulation or active matrix (AM) liquid crystal formulation respectively to analyze their dielectric anisotropy. A composition of the active matrix (AM) liquid crystal formulation (AM1; JM-2069-054) is shown in Table 2.

TABLE 2

| Active liquid crystal formulation AM1 (JM-2069-054) | |
|---|---|
| Liquid crystal monomer | Concentration (wt %) |
| C₄H₉-[cyclohexyl]-[cyclohexyl]-[phenyl(3,4,5-trifluoro)] | 11 wt % |
| C₃H₇-[cyclohexyl]-[phenyl]-[phenyl(3,4,5-trifluoro)] | 43 wt % |

TABLE 2-continued

| Active liquid crystal formulation AM1 (JM-2069-054) | |
|---|---|
| Liquid crystal monomer | Concentration (wt %) |
| 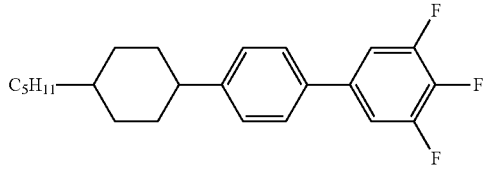 | 24 wt % |
| 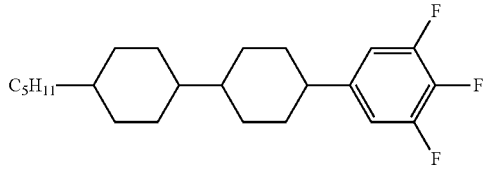 | 11 wt % |
| 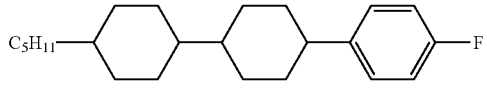 | 4 wt % |
| 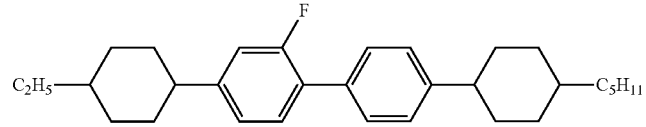 | 5 wt % |

In addition, a composition of the passive matrix (PM) liquid crystal formulation (PM1; IBL-087c) is shown in Table 3.

TABLE 3

| Passive liquid crystal formulation PM1 (IBL-087c) | |
|---|---|
| Monomer | Concentration (wt %) |
| 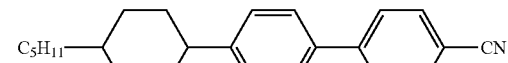 | 15 wt % |
| 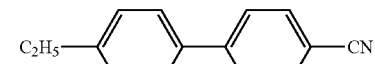 | 14 wt % |
| 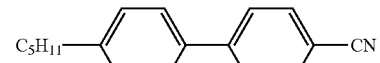 | 34 wt % |
| 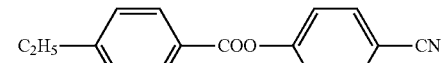 | 13 wt % |
| 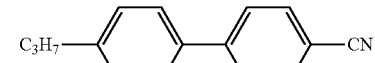 | 15 wt % |
| 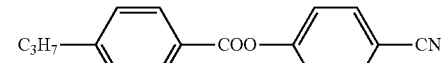 | 10 wt % |

The liquid crystal compounds in Example 1 to 4 were added into a passive matrix (PM) liquid crystal formulation or active matrix (AM) liquid crystal formulation respectively, wherein each liquid crystal formulation contained 10 wt % of the liquid crystal compound. A refractive index detector (DR-M2) was used to detect the birefringence. A Liquid Crystal Analysis System (LCAS-1) was used to detect the dielectric anisotropy and calculate the birefringence (Δn) and dielectric anisotropy (Δ∈) of each liquid crystal compound. Furthermore, a Differential Scanning calorimetry (DSC) was also used to detect the melting point ($T_c$), and a Viscometer (CAP1000L) was used to detect the viscosity (η) Table 4 shows the features of the liquid crystal formulation after adding different liquid crystal compounds. In addition, Table 5 shows the dielectric anisotropy (Δ∈) of each liquid crystal compound calculated by LCAS-1.

TABLE 4

Liquid crystal compounds in the liquid crystal formulation

| | Δn | Δ∈ | Increase of Δ∈ | $T_c$ (° C.) | η (at 20° C.) |
|---|---|---|---|---|---|
| LC (PM1) | 0.24 | 17.8 | — | 97.6 | 48 |
| LC (PM1) + Example 1 | 0.22 | 21.2 | 19.1% | 90.1 | 55 |
| LC (PM1) + Example 2 | 0.22 | 22.5 | 26.4% | 92.7 | 57 |
| LC (PM1) + Example 3 | 0.22 | 22.6 | 26.9% | 92.6 | 58 |
| LC (PM1) + Example 4 | 0.22 | 22.1 | 24.1% | 94.3 | 62 |
| LC (PM1) + Comparative Example 1 | 0.24 | 18.6 | 4.5% | 100.3 | 45 |
| LC (PM1) + Comparative Example 2 | 0.22 | 18.9 | 6.2% | 97.2 | 50 |
| LC (AM1) | 0.15 | 12.5 | — | 99.4 | 37 |
| LC (AM1) + Example 1 | 0.16 | 17.3 | 38.4% | 95.3 | 45 |
| LC (AM1) + Example 2 | 0.16 | 19.4 | 55.2% | 97.9 | 49 |
| LC (AM1) + Example 3 | 0.16 | 19.6 | 56.8% | 97.5 | 49 |
| LC (AM1) + Example 4 | 0.16 | 19.0 | 52.0% | 98.7 | 52 |
| LC (AM1) + Comparative Example 1 | 0.17 | 13.9 | 11.2% | 109.7 | 51 |
| LC (AM1) + Comparative Example 2 | 0.16 | 14.7 | 17.6% | 103.3 | 45 |

TABLE 5

Dielectric anisotropy of liquid crystal compounds

| | Example 1 (PM1) | Example 2 (PM1) | Example 3 (PM1) | Example 4 (PM1) | Comparative Example 1 (PM1) | Comparative Example 2 (PM1) |
|---|---|---|---|---|---|---|
| Δ∈ | 52 | 65 | 66 | 61 | 26 | 29 |

| | Example 1 (AM1) | Example 2 (AM1) | Example 3 (AM1) | Example 4 (AM1) | Comparative Example 1 (AM1) | Comparative Example 2 (AM1) |
|---|---|---|---|---|---|---|
| Δ∈ | 60 | 82 | 83 | 77 | 27 | 35 |

Referring to Table 5, although the structures of the compounds in the Comparative Examples 1 and 2 were similar to the structures in Examples 1-4, the dielectric anisotropy of the compounds in the Comparative Examples 1 and 2 were both quite low. Therefore, when the compounds in the Comparative Examples 1 or 2 was added into the active or passive liquid crystal formulations, the dielectric anisotropy of the entire liquid crystal formulation only increased a little. That is, if the compound in the Comparative Examples 1 or 2 is used in a liquid crystal display, the driving voltage of the display may not decrease effectively.

On the contrary, all the compounds in the Examples 1-4 had high dielectric anisotropy. Therefore, when the compounds in the Examples 1-4 was added into the active or passive liquid crystal formulations respectively, the dielectric anisotropy of the entire liquid crystal formulation increased markedly. That is, if the compounds in the Examples 1-4 are used in a liquid crystal display, the driving voltage of the display may decrease effectively.

Example 9

Additive Amount of the Liquid Crystal Compound 1

Table 6 shows the result of adding different amounts of the liquid crystal compound 1 in Example 1 to the active or passive liquid crystal formulation. Table 7 shows the dielectric anisotropy of the liquid crystal compound 1 (Example 1) calculated by LCAS-1. The active or passive liquid crystal formulation respectively contains 5 wt %, 10 wt %, or 15 wt % of the liquid crystal compound in Example 1.

TABLE 6

Liquid crystal compound 1 in liquid crystal formulation

| | Δn | Δ∈ | Increment of Δ∈ | $T_c$ (° C.) | η (at 20° C.) |
|---|---|---|---|---|---|
| LC (PM1) | 0.24 | 17.8 | — | 97.6 | 48 |
| LC (PM1) + Example 1 (5 wt %) | 0.22 | 19.2 | 7.8% | 91.8 | 50 |
| LC (PM1) + Example 1 (10 wt %) | 0.22 | 21.2 | 19.7% | 90.1 | 55 |
| LC (PM1) + Example 1 (15 wt %) | 0.23 | 22.9 | 28.6% | 88.9 | 61 |
| LC (AM1) | 0.15 | 12.5 | — | 99.4 | 37 |
| LC (AM1) + Example 1 (5 wt %) | 0.15 | 14.7 | 17.6% | 96.9 | 43 |
| LC (AM1) + Example 1 (10 wt %) | 0.16 | 17.3 | 38.4% | 95.3 | 45 |
| LC (AM1) + Example 1 (15 wt %) | 0.16 | 19.2 | 52.8% | 94.2 | 50 |

TABLE 7

Dielectric anisotropy of liquid crystal compound 1

| Sample | Example 1 (PM1) 5 wt % | Example 1 (PM1) 10 wt % | Example 1 (PM1) 15 wt % | Example 1 (AM1) 5 wt % | Example 1 (AM1) 10 wt % | Example 1 (AM1) 15 wt % |
|---|---|---|---|---|---|---|
| Δ∈ | 46 | 52 | 52 | 56 | 60 | 56 |

Referring to Table 7, the liquid crystal compound 1 (Example 1) had good dielectric anisotropy and solubility for both of the active and passive liquid crystal formulations. In addition, when the additive amount of the liquid crystal compound 1 increased, the dielectric anisotropy of the entire liquid crystal formulation increased markedly.

Example 10

Additive Amount of the Liquid Crystal Compound 2

Table 8 shows the result of adding different amounts of the liquid crystal compound 2 (Example 2) to the active or passive liquid crystal formulation. Table 9 shows the dielectric anisotropy of the liquid crystal compound 2 (Example 2) calculated by LCAS-1. The active or passive liquid crystal formulation respectively contains 5 wt %, 10 wt %, or wt % of the liquid crystal compound 2 (Example 2).

TABLE 8

Liquid crystal compound 2 in liquid crystal formulation

| | Δn | Δε | Increment of Δε | $T_c$ (° C.) | η (at 20° C.) |
|---|---|---|---|---|---|
| LC (PM1) | 0.24 | 17.8 | — | 97.6 | 48 |
| LC (PM1) + Example 2 (5 wt %) | 0.22 | 20.1 | 12.9% | 94.3 | 51 |
| LC (PM1) + Example 2 (10 wt %) | 0.22 | 22.5 | 26.4% | 92.7 | 57 |
| LC (PM1) + Example 2 (15 wt %) | 0.23 | 24.5 | 37.6% | 90.2 | 65 |
| LC (AM1) | 0.15 | 12.5 | — | 99.4 | 37 |
| LC (AM1) + Example 2 (5 wt %) | 0.15 | 15.8 | 26.4% | 98.5 | 42 |
| LC (AM1) + Example 2 (10 wt %) | 0.16 | 19.4 | 55.2% | 97.9 | 49 |
| LC (AM1) + Example 2 (15 wt %) | 0.16 | 22.6 | 80.8% | 97.4 | 57 |

TABLE 9

Dielectric anisotropy of liquid crystal compound 2

| Sample | Example 2 (PM1) 5 wt % | Example 2 (PM1) 10 wt % | Example 2 (PM1) 15 wt % | Example 2 (AM1) 5 wt % | Example 2 (AM1) 10 wt % | Example 2 (AM1) 15 wt % |
|---|---|---|---|---|---|---|
| Δε | 62 | 65 | 62 | 80 | 82 | 80 |

Referring to Table 9, the liquid crystal compound 2 (Example 2) had good dielectric anisotropy and solubility for both of the active and passive liquid crystal formulations. In addition, when the additive amount of the liquid crystal compound 2 increased, the dielectric anisotropy of the entire liquid crystal formulation increased markedly.

Furthermore, Tables 10 and 11 shows the dielectric anisotropy of liquid crystal compounds in the Examples 1-4 and Comparative Examples 1-2. As shown in Table 10, the liquid crystal compounds in the Examples 1-4 had higher dielectric anisotropy, wherein the passive liquid crystal formulation contained 5 wt %, 10 wt %, and 15 wt % of the liquid crystal compound respectively. As shown in Table 11, the liquid crystal compounds in the Examples 1-4 had higher dielectric anisotropy, wherein the active liquid crystal formulation contained 5 wt %, 10 wt %, and 15 wt % of the liquid crystal compound respectively.

TABLE 10

Dielectric anisotropy of liquid crystal compounds at various concentration in the passive liquid crystal formulation

| | Example 1 | | | Comparative Example 1 | | | Comparative Example 2 | | |
|---|---|---|---|---|---|---|---|---|---|
| Conc. | 5 wt % | 10 wt % | 15 wt % | 5 wt % | 10 wt % | 15 wt % | 5 wt % | 10 wt % | 15 wt % |
| Δε | 19.2 | 21.2 | 22.9 | 18.2 | 18.6 | 18.9 | 18.6 | 18.9 | 19.8 |

TABLE 11

Dielectric anisotropy of liquid crystal compounds at various concentration in the active liquid crystal formulation

| | Example 1 | | | Comparative Example 1 | | | Comparative Example 2 | | |
|---|---|---|---|---|---|---|---|---|---|
| Conc. | 5 wt % | 10 wt % | 15 wt % | 5 wt % | 10 wt % | 15 wt % | 5 wt % | 10 wt % | 15 wt % |
| Δε | 14.7 | 17.3 | 19.2 | 13.6 | 13.9 | 16.0 | 14.1 | 14.7 | 16.4 |

Example 11

Driving Voltage

Liquid crystal compounds in the Examples 1-2 and Comparative Examples 1-2 were added into the passive liquid crystal formulation PM1 (IBL-087c) and active liquid crystal formulation AM1(JM-2069-054) to form liquid crystal displays. The driving voltages of the liquid crystal displays were measured (Table 12).

TABLE 12

Driving voltage of the liquid crystal displays

| | Conc. (wt %) | Δε of liquid crystal compound | Driving voltage (Vth) | Decrease of driving voltage (%) |
|---|---|---|---|---|
| LC (PM1) | — | — | 1.22 | — |
| LC (PM1) + Example 1 | 15 wt % | 52 | 0.98 | 16.3% |
| LC (PM1) + Example 2 | 15 wt % | 62 | 0.94 | 18.6% |
| LC (PM1) + comparative Example 1 | 15 wt % | 29 | 1.13 | 7.5% |
| LC (PM1) + comparative Example 2 | 15 wt % | 35 | 1.12 | 8.3% |
| LC (AM1) | — | — | 1.65 | — |
| LC (AM1) + Example 1 | 15 wt % | 56 | 1.15 | 25.7% |
| LC (AM1) + Example 2 | 15 wt % | 79 | 1.09 | 28.1% |
| LC (AM1) + Comparative Example 1 | 15 wt % | 35 | 1.46 | 11.5% |
| LC (PM1) + Comparative Example 2 | 15 wt % | 38 | 1.38 | 16.3% |

As shown in Table 12, when the liquid crystal compounds 1 and 2 (Examples 1 and 2) were used in the liquid crystal displays respectively, the driving voltages of the liquid crystal displays decreased effectively. However, conventional liquid crystal compounds as in Comparative Examples 1 and 2 could not effectively decrease the driving voltage of the liquid crystal displays.

Example 12

Dielectric Anisotropy of Liquid Crystal Compounds in Example 1 and 5-7

The liquid crystal compounds in Example 1 and 5-7 were added into a passive matrix liquid crystal formulation PM2, an active matrix liquid crystal formulation AM1, or a blue phase liquid crystal formulation BM1 respectively to analyze their dielectric anisotropy. The composition of the active matrix liquid crystal formulation AM1 (JM-2069-054) is shown in Example 8. The composition of the passive matrix liquid crystal formulation PM2 (KC-0202-159) is shown in Table 13. The composition of the blue phase liquid crystal formulation BM1 (JM-2069-145) is shown in Table 14.

TABLE 13

Passive liquid crystal formulation PM2 (KC-0202-159)

| Liquid crystal monomer | Concentration (wt %) |
| --- | --- |
| C$_5$H$_{11}$—⌬—⌬—⌬—CN | 21 wt % |
| C$_2$H$_5$—⌬—⌬—CN | 7 wt % |
| C$_3$H$_7$—⌬—⌬—CN | 16 wt % |
| C$_2$H$_5$—⌬—COO—⌬—CN | 11 wt % |
| C$_3$H$_7$—⌬—⌬—COO—⌬(F)—CN | 15 wt % |
| C$_3$H$_7$—⌬—COO—⌬(F)—CN | 13 wt % |
| H$_{11}$C$_5$—⌬—⌬—C(=O)O—⌬—CN | 17 wt % |

TABLE 14

Blue phase liquid crystal formulation BM1 (JM-2069-145)

| Monomer | Concentration (wt %) |
| --- | --- |
| C$_5$H$_{11}$—⌬—⌬—COO—⌬(F)—CN | 16 wt % |
| C$_5$H$_{11}$—⌬—⌬—CN | 14 wt % |
| C$_3$H$_7$—⌬—⌬—CN | 13 wt % |
| C$_4$H$_9$—⌬—COO—⌬(F)—CN | 7 wt % |

TABLE 14-continued

Blue phase liquid crystal formulation BM1 (JM-2069-145)

| Monomer | Concentration (wt %) |
|---|---|
| $C_5H_{11}$—⌬—COO—⌬(F)—CN | 12 wt % |
| $C_5H_{11}$—⌬—C(=O)O—⌬(F,F)—CN | 10 wt % |
| $C_3H_7$—⌬—⌬—C(=O)O—⌬(F,F)—CN | 27 wt % |

The liquid crystal compounds 1, 5, and 22 in Examples 1, 5, and 7 were added into the passive matrix liquid crystal formulation PM2, active matrix liquid crystal formulation AM1, or blue phase liquid crystal formulation BM1 respectively, wherein each liquid crystal formulation contained 5 wt % of the liquid crystal compound. A refractive index detector (DR-M2) was used to detect the birefringence. A Liquid Crystal Analysis System (LCAS-1) was used to detect the dielectric anisotropy and calculate the birefringence ($\Delta n$) and dielectric anisotropy ($\Delta \in$) of each liquid crystal compound. Furthermore, a Differential Scanning calorimetry (DSC) was also used to detect the melting point ($T_c$), and a Viscometer (CAP1000L) was used to detect the viscosity ($\eta$).

In addition, after the liquid crystal compounds in Examples 1 and 5-7 were added into the formulation described above to form liquid crystal displays, the driving voltages of them were measured. Table 15 shows various features after adding different liquid crystal compounds into the liquid crystal formulations. In addition, Table 16 shows the dielectric anisotropy ($\Delta \in$) of each liquid crystal compound calculated by LCAS-1.

TABLE 15

Liquid crystal compounds in various liquid crystal formulation

| | $\Delta n$ | $\Delta \in$ | Increment of $\Delta \in$ | Driving Voltage (Vth) | $T_c$ (° C.) | $\eta$ (at 20° C.) |
|---|---|---|---|---|---|---|
| LC (PM2) | 0.23 | 25.5 | — | 0.93 | 95.1 | 74 |
| LC(PM2) + Example 1 | 0.23 | 27.3 | 7.0% | 0.89 | 93.5 | 77 |
| LC(PM2) + Example 5 | 0.23 | 27.6 | 8.2% | 0.86 | 91.6 | 76 |
| LC(PM2) + Example 6 | 0.23 | 25.9 | 1.6% | 0.91 | 90.8 | 77 |
| LC(PM2) + Example 7 | 0.23 | 28.1 | 10.1% | 0.81 | 93.3 | 82 |
| LC (AM1) | 0.15 | 12.5 | — | 1.65 | 99.4 | 37 |
| LC(AM1) + Example 1 | 0.15 | 14.7 | 17.6% | 1.37 | 96.9 | 43 |
| LC(AM1) + Example 5 | 0.15 | 15.1 | 20.8% | 1.31 | 93.9 | 42 |
| LC(AM1) + Example 6 | 0.15 | 14.3 | 14.4% | 1.39 | 93.8 | 42 |
| LC(AM1) + Example 7 | | | Precipitated | | | |
| LC (BM1) | 0.22 | 33.6 | — | 0.69 | 80.8 | 80 |
| LC(BM1) + Example 1 | 0.22 | 34.7 | 3.2% | 0.65 | 79.3 | 83 |
| LC(BM1) + Example 5 | 0.22 | 35.5 | 5.7% | 0.61 | 77.8 | 82 |
| LC(BM1) + Example 6 | 0.22 | 34.2 | 1.9% | 0.67 | 75.6 | 80 |
| LC(BM1) + Example 7 | 0.22 | 36.0 | 7.1% | 0.58 | 78.8 | 85 |

TABLE 16

Dielectric anisotropy of liquid crystal compounds

| | Example 1 (PM2) | Example 5 (PM2) | Example 6 (PM2) | Example 7 (PM2) |
|---|---|---|---|---|
| $\Delta n$ | 0.22 | 0.20 | 0.21 | 0.25 |
| $\Delta \in$ | 60 | 67 | 33 | 77 |

| | Example 1 (AM1) | Example 5 (AM1) | Example 6 (AM1) | Example 7 (AM1) |
|---|---|---|---|---|
| $\Delta n$ | 0.22 | 0.22 | 0.22 | — |
| $\Delta \in$ | 56 | 64 | 48 | — |

| | Example 1 (BM1) | Example 5 (BM1) | Example 6 (BM1) | Example 7 (BM1) |
|---|---|---|---|---|
| $\Delta n$ | 0.22 | 0.22 | 0.22 | 0.22 |
| $\Delta \in$ | 55 | 64 | 46 | 79 |

As shown in Table 4 and Table 15, the liquid crystal compounds in various Examples had a higher dielectric anisotropy compared to the liquid crystal compounds in the Comparative Examples. For example, the liquid crystal compounds in Examples 5 and 7 having several F substitutions, had a dielectric anisotropy of above 60. Therefore, if these liquid crystal compounds were added into a liquid crystal formulation, the total dielectric anisotropy would increased and the driving voltage of the liquid crystal display would effectively decrease.

In addition, according to the Examples described above, when $R_1$ and/or $R_2$ in formula (I) or $X_1$ and/or $X_2$ in formula (II) was/were F, the dielectric anisotropy can be increased and reach above 40, or between 40 and 85. In some Examples, the dielectric anisotropy even reached above 45, or between 45 and 85. In some Examples, the concentration of liquid crystal compounds in the liquid crystal layer were between about 1 wt % and 20 wt %, or between about 5 wt % and 15 wt %.

While the disclosure has been described by way of example and in terms of the preferred embodiments, it is to be understood that the disclosure is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A liquid crystal compound having the following formula:

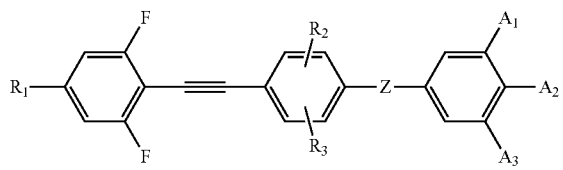

wherein $A_1$, $A_2$, and $A_3$ are independently hydrogen, halogen, cyano, thiocyanato, or —$OCF_3$;
$R_1$ is hydrogen, halogen, $C_1$-$C_{12}$ alkyl, $C_1$-$C_{12}$ alkoxy, $C_1$-$C_{12}$ haloalkly, $C_2$-$C_{12}$ alkenyl, or $C_2$-$C_{12}$ alkynyl;
$R_2$ and $R_3$ are independently halogen, $C_1$-$C_6$ alkyl, $C_1$-$C_6$ haloalkly, cyano, thiocyanato, or —$OCF_3$; and
Z is a single bond, —O—, —$CH_2O$—, —C(O)O—, —OCO—, —C(O)NH—, or —CH=CH—.

2. The liquid crystal compound as claimed in claim 1, wherein the liquid crystal compound has the following formula:

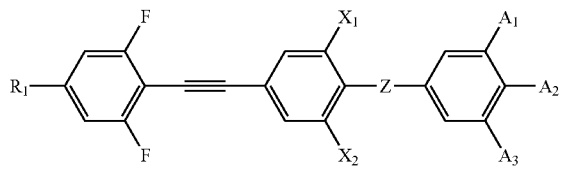

wherein $A_1$, $A_2$, and $A_3$ are independently hydrogen, halogen, cyano, thiocyanato, or —$OCF_3$;
$R_1$ is hydrogen, halogen, $C_1$-$C_{12}$ alkyl, $C_1$-$C_{12}$ alkoxy, $C_1$-$C_{12}$ haloalkly, $C_2$-$C_{12}$ alkenyl, or $C_2$-$C_{12}$ alkynyl;
$X_1$, $X_2$ are independently fluorine, cyano, thiocyanato, or —$OCF_3$; and
Z is a single bond, —O—, —$CH_2O$—, —C(O)O—, —OCO—, —C(O)NH—, or —CH=CH—.

3. The liquid crystal compound as claimed in claim 2, wherein the liquid crystal compound has the following formula:

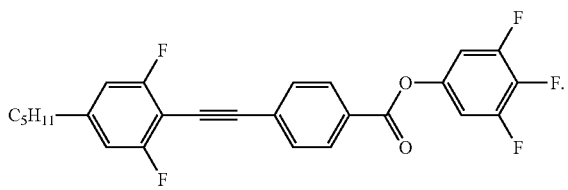

4. The liquid crystal compound as claimed in claim 2, wherein the liquid crystal compound has the following formula:

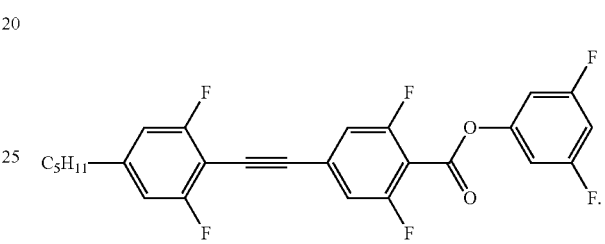

5. The liquid crystal compound as claimed in claim 2, wherein the liquid crystal compound has the following formula:

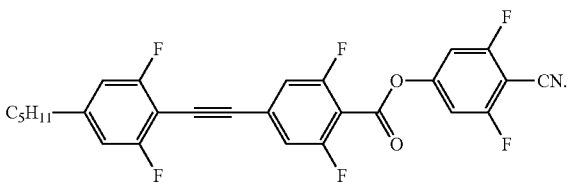

6. The liquid crystal compound as claimed in claim 1, wherein a dielectric anisotropy (Δ∈) of the liquid crystal compound is larger than 45.

7. A liquid crystal display, comprising:
a first substrate;
a second substrate disposed opposite to the first substrate; and
a liquid crystal layer disposed between the first substrate and the second substrate, wherein the liquid crystal layer comprises the liquid crystal compound as claimed in claim 1.

* * * * *